United States Patent
Raja et al.

(10) Patent No.: US 9,447,023 B2
(45) Date of Patent: Sep. 20, 2016

(54) CURCUMIN AND TETRAHYDROCURCUMIN DERIVATIVES

(71) Applicants: Krishnaswami Raja, Staten Island, NY (US); Probal Banerjee, Staten Island, NY (US); Andrew Auerbach, Livingston, NJ (US); Wei Shi, Staten Island, NY (US); William L'Amoreaux, Freehold, NJ (US)

(72) Inventors: Krishnaswami Raja, Staten Island, NY (US); Probal Banerjee, Staten Island, NY (US); Andrew Auerbach, Livingston, NJ (US); Wei Shi, Staten Island, NY (US); William L'Amoreaux, Freehold, NJ (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 13/942,606

(22) Filed: Jul. 15, 2013

(65) Prior Publication Data
US 2013/0296527 A1 Nov. 7, 2013

Related U.S. Application Data

(63) Continuation of application No. 12/445,356, filed as application No. PCT/US2007/021805 on Oct. 12, 2007, now Pat. No. 8,487,139.

(60) Provisional application No. 60/829,185, filed on Oct. 12, 2006.

(51) Int. Cl.
| | |
|---|---|
| A61K 8/37 | (2006.01) |
| A61K 8/39 | (2006.01) |
| A61Q 19/02 | (2006.01) |
| C07C 229/12 | (2006.01) |
| C07C 247/04 | (2006.01) |
| C07C 49/248 | (2006.01) |
| C07C 49/255 | (2006.01) |
| C07C 69/52 | (2006.01) |
| C07C 69/02 | (2006.01) |
| A61K 8/49 | (2006.01) |
| A61K 8/81 | (2006.01) |
| C07D 249/04 | (2006.01) |
| C07C 69/602 | (2006.01) |

(52) U.S. Cl.
CPC .............. *C07C 229/12* (2013.01); *A61K 8/37* (2013.01); *A61K 8/39* (2013.01); *A61K 8/496* (2013.01); *A61K 8/8147* (2013.01); *A61Q 19/02* (2013.01); *C07C 49/248* (2013.01); *C07C 49/255* (2013.01); *C07C 69/52* (2013.01); *C07C 69/602* (2013.01); *C07C 247/04* (2013.01); *C07D 249/04* (2013.01); *A61K 2800/522* (2013.01); *A61K 2800/56* (2013.01)

(58) Field of Classification Search
CPC ................. A61K 2800/522; A61K 2800/56; A61K 8/37; A61K 8/39; A61Q 19/02; C07C 229/12; C07C 247/04; C07C 49/248; C07C 49/255; C07C 69/52; C07C 69/602
See application file for complete search history.

(56) References Cited

U.S. PATENT DOCUMENTS

| | | | |
|---|---|---|---|
| 2004/0014721 A1 | 1/2004 | Hensley et al. | |
| 2005/0187255 A1* | 8/2005 | Lee .................. | C07C 49/248 514/332 |
| 2010/0240905 A1* | 9/2010 | Raja et al. ............... | 548/255 |

FOREIGN PATENT DOCUMENTS

| | | | |
|---|---|---|---|
| EP | WO 2004/031122 | * | 4/2004 |
| WO | 0202582 | | 1/2002 |
| WO | 2004031122 | | 4/2004 |
| WO | 2008051474 | | 5/2008 |

OTHER PUBLICATIONS

Sharma et al. (European J. Cancer; 41 (2005) 1955-1968).*
Fujisawa et al., Dimerization, ROS formation, and biological activity of o-methoxyphenols, Arch. Immunol. Ther. Exp., 2005, vol. 53, pp. 28-38.
Mizushina et al., Monoacetylcurcumin: A new inhibitor of eukaryotic DNA polymerase lambda and a new ligand for inhibitor-affinity chromatography, Biochemical and Biophysical Research Communication, 2005, vol. 337, pp. 1288-1295.
Shi et al., Synthesis of Monofunctional Curcumin Derivatives, Clicked Curcumin Dimer, and a PAMAM Dendrimer Curcumin Conjugate for Therapeutic Applications, Organic Letters, 2007, vol. 9, No. 26, pp. 5461-5464.

(Continued)

*Primary Examiner* — Valerie Rodriguez-Garcia
(74) *Attorney, Agent, or Firm* — Hoffmann & Baron, LLP

(57) ABSTRACT

The invention relates to novel curcumin and tetrahydrocurcumin derivatives, which have been modified at one phenolic group to incorporate more-reactive groups. The curcumin and tetrahydrocurcumin derivatives are in the form of monomers, dimmers, and polymers.

$$Z\text{-}L_n\text{-}Y \tag{I}$$

wherein: Z is represented by:

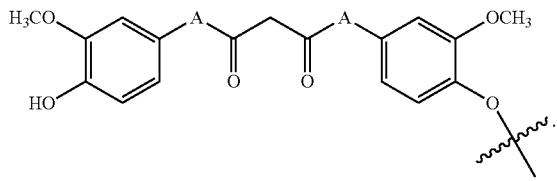

14 Claims, No Drawings

(56) References Cited

OTHER PUBLICATIONS

Shiv Kumar Dubey et al., Novel method for Preaparation of monoesters of Symmetric Diphenolic Compounds Like Curcumin (1,7-Bis(4-hydroxy-3-methoxy phenyl)-1,6-heptadiene-3,5-dione) via Solid-Phase Synthesis, vol. 37, No. 23 (2007), XP009148714.

Shiv K. Dubey et al., Design, Synthesis and Characterization of Some Bioactive Conjugates of Curcumin with Glycine, Glutamic Acid, Valine and Demethylenated Piperic Acid and Study of Their Antimicrobial and Antiproliferative Properties, vol. 43, No. 9 (2007), XP002639535.

* cited by examiner

CURCUMIN AND TETRAHYDROCURCUMIN DERIVATIVES

CROSS-REFERENCE TO RELATED APPLICATION

This application is a continuation of U.S. patent application Ser. No. 12/445,356, filed on Jun. 7, 2010, which is the national stage of PCT Application No. PCT/US2007/021805, filed on Oct. 12, 2007, which in turn claims the benefit of U.S. Provisional Application No. 60/829,185, filed Oct. 12, 2006, all of which are incorporated herein by reference.

BACKGROUND OF THE INVENTION

*Curcuma longa* commonly referred to as turmeric is used in south Asian cooking, as a cosmetic, and in the ancient Ayurvedic system of medicine. The Banerjee lab at College of Staten Island and other groups have established that curcumin (1Z,6Z)-1,7-bis(4-hydroxy-3-methoxyphenyl) hepta-1,6-diene 3,5-dione, the primary active ingredient in turmeric, has potent anticancer properties. Curcumin exerts its anticancer effect through the suppression of NF-k$\beta$. Curcumin mediates its therapeutic effect by regulating the transcription factor NF-k$\beta$ and NF-k$\beta$ regulated gene products COX-2, cyclin D1, adhesion molecules, MMPs, inducible nitric oxide synthase, Bcl-XL, Bcl-2 and TNF.

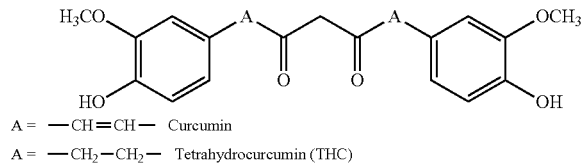

A = —CH=CH—  Curcumin
A = —CH$_2$—CH$_2$—  Tetrahydrocurcumin (THC)

Curcumin has two phenolic groups, which can be used for chemical modification. Most curcumin derivatives reported in literature are symmetric in that both the phenolic groups have been chemically modified in the same way. Rare exceptions have been reported. For example, the Mizushina, et al. reference [5] reported the use of monoacetylcurcumin as an inhibitor of eukaryotic DNA polymerase $\lambda$ and as a ligand for inhibitor-affinity chromatography. See Mizushina, et al. Monoacetylcurcumin: A new inhibitor of eukaryotic DNA polymerase and a new ligand for inhibitor-affinity chromatography, *Biochemical and Biophysical Research Communications* (2005) 337, 1288-1295. The utility of monoacetylcurcumin is limited since it does not contain a reactive group at the phenolic position.

One of the major limitations of unmodified curcumin is its poor water and plasma solubility. A recent study has shown that even doses as high as 8 g of curcumin per day administered to human subjects result in an average peak serum concentration of only 652.5 ng/ml [9]. There is a need for curcumin derivatives that have improved water solubility and that still maintain their biological activity. For example, unmodified phenolic groups, in many cases, are responsible for beneficial antioxidant properties.

U.S. Pat. No. 5,861,415 describes a bioprotectant composition containing curcuminoids, their method of use and extraction processes for obtaining them. Curcuminoids were found to have anti-oxidant, anti-inflammatory, antibacterial, antifungal, ant parasitic, antimutagen, anticancer, and detox properties. U.S. Pat. No. 5,891,924 describes a method of inhibiting the activation of NF kappa B transcription factor using curcumin. U.S. Pat. No. 6,653,327 describes a cross-regulin composition of tumeric derived tetrahydrocurcumin (THC) for skin lightening and protection against UVB rays. U.S. Pat. No. 6,887,898 describes tumeric extracts to be effective in treating beta-Amyloid protein-induced disease.

SUMMARY OF THE INVENTION

In one embodiment, the invention related to a curcumin derivative having the formula I:

$$Z-L_n-Y \qquad (I)$$

wherein:
Z is represented by:

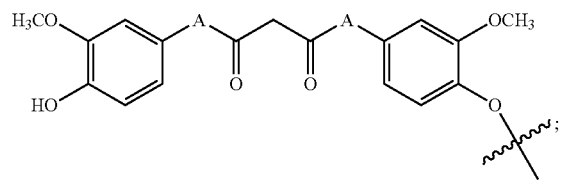

A is —CH$_2$—CH$_2$— or —CH=CH—;
L is —[C(O)]$_{n1}$—R$^1$—;
n is 0 or 1;
n1 is 0 or 1;
R$^1$ is R$^2$, R$^{3a}$, R$^4$, or R$^5$;
R$^2$ is a saturated or unsaturated, branched or unbranched hydrocarbyl with 1 to 18 carbon atoms;
R$^{3a}$ is —(CH$_2$—CH$_2$—O)$_{n2}$—;
R$^{3b}$ is —(O—CH$_2$—CH$_2$)$_{n2}$—;
n2 is an integer between 1 and 2,000;
R$^4$ is —R$^2$—R$^{3a}$—, —R$^2$—R$^{3b}$—, or —R$^{3a}$—R$^2$—;
R$^5$ is —R$^9$—R$^6$—R$^9$—;
R$^6$ is —C(O)—NH—R$^{3a}$—;
Y is —CH=CH—C(O)OR$^8$, —CH=C(CH$_3$)—C(O)OR$^8$, —COOR$^7$, —N$_3$, —C≡C—R$^8$, —NH$_2$, —CHO, —OH, -epoxide-R$^8$, —SH, or -maleimide;
with the proviso that when L is 0, Y is —CH=CH—C(O)OR$^8$ or —CH=C(CH$_3$)—C(O)OR$^8$;
with the proviso that when R$^1$ is R$^{3a}$ or —R$^2$—R$^{3a}$—, Y is —CH=CH—C(O)OR$^8$ or —CH=C(CH$_3$)—C(O)OR$^8$;
R$^7$ is hydrogen, C$_{1-4}$ alkyl, or a moiety such that —COOR$^7$ is an activated ester;
R$^8$ is hydrogen or C$_{1-4}$ alkyl; and
R$^9$ is independently C$_{1-4}$ alkyl.

In another embodiment, the invention relates to a curcumin dimer having the formula II:

$$Z^a-L^a-Y^a-(L^b)_{n3}-Y^b-L^c-Z^b \qquad (II)$$

wherein:
$Z^a$ and $Z^b$ are represented by

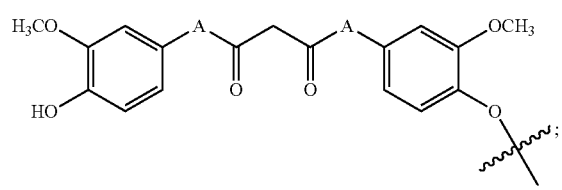

A is independently —CH$_2$—CH$_2$— or —CH=CH—;
$L^a$, $L^b$, and $L^c$ are independently —[C(O)]$_{n1}$—R$^{1a}$—;
n1 is independently 0 or 1;
R$^{1a}$ is independently R$^2$, R$^{4a}$ or R$^5$;

$R^2$ is independently a saturated or unsaturated, branched or unbranched hydrocarbyl with 1 to 18 carbon atoms;

$R^{3a}$ is —$(CH_2$—$CH_2$—$O)_{n2}$—;

$R^{3b}$ is —$(O$—$CH_2$—$CH_2)_{n2}$—;

n2 is independently an integer between 1 and 2,000;

$R^{4a}$ is —$R^2$—$R^{3b}$— or —$R^{3a}$—$R^2$—;

$R^5$ is —$R^9$—$R^6$—$R^9$—;

$R^6$ is —$C(O)$—$NH$—$R^{3a}$—;

$Y^a$ and $Y^b$ are independently —$COOR^9$—, -triazolyl-, —$NH$—, —$O$—, or —$S$—$S$—;

$R^9$ is $C_{1-4}$ alkyl;

n3 is independently 0 or 1;

when n3 is 0, $Y^a$ and $Y^b$ are modified so that at least one covalent bond is formed between $Y^a$ and $Y^b$, and when n3 is 1, $L^b$ is modified so that at least one covalent bond is formed between $L^b$ and both $Y^a$ and $Y^b$.

DETAILED DESCRIPTION

The invention relates to novel curcumin derivatives in which one of the phenolic groups has been modified.

In one aspect of the invention, the curcumin derivative is represented by formula I, i.e., $Z$-$L_n$-$Y$. In formula I, Z represents:

A represents —$CH_2$—$CH_2$— or —$CH$=$CH$—. When A is —$CH_2$—$CH_2$—, $Z$-$L_n$-$Y$ is a tetrahydrocurcumin derivative. When A is —$CH$=$CH$—, $Z$-$L_n$-$Y$ is a curcumin derivative.

L is a linker represented by —$[C(O)]_{n1}$—$R^1$—. The letter n is 0 or 1. When n is 0, there is no linker. The letter n1 is 0 or 1. For example, when n1 is 1, L is When n1 is 0, then L is —$R^1$—.

$R^1$ is represented by $R^2$, $R^{3a}$, $R^4$, or $R^5$. $R^2$ is a hydrocarbyl chain with 1 to 18 carbon atoms. Hydrocarbyl chains are saturated or unsaturated, and branched or unbranched. The carbon atoms of a chain can all be saturated, or can all be unsaturated. Alternatively, the chain can comprise a mixture of saturated and unsaturated carbon atoms. The unsaturated hydrocarbyl chains contain one or more double and/or triple bonds.

Some examples of suitable, saturated straight-chained hydrocarbyl chains include methyl, ethyl, n-propyl, n-butyl, n-pentyl, n-hexyl, dodecyl, hexadecyl, and octadecyl chains. Preferred straight chain alkyl groups include methyl and ethyl. Some examples of suitable, unsaturated straight-chained hydrocarbyl chains include 3-butenyl, 1,3-heptadienyl, 2-dodecynyl, oleyl, linoleyl, and linolenyl chains.

Some examples of suitable saturated, branched alkyl groups include iso-propyl, iso-butyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl (neopentyl), 1-methylpentyl, 2-methylpentyl, 3-methylpentyl, 4-methylpentyl groups, and 2-methyl, 5-ethyldecyl. Preferred branched alkyl groups include isopropyl and t-butyl. Some suitable examples of unsaturated, branched alkyl groups include 1-methyl-4-pentenyl and 7-ethyl-10,15-hexadecadienyl.

$R^{3a}$ is represented by —$(CH_2$—$CH_2$—$O)_{n2}$—, and $R^{3b}$ is —$(O$—$CH_2$—$CH_2)_{n2}$—. $R^{3a}$ and $R^{3b}$ represent polyethylene glycol chains. The variable n2 is an integer with a minimum value of one, two, or three. The maximum value of n2 is four, twelve, fifty, or 2,000. Preferably, the maximum value of n2 is fifty, and more preferably twelve. For example, if n2 is ten, then $R^{3a}$ is a polyethylene glycol polymer with ten ethylene glycol units.

The variable $R^4$ is represented by —$R^2$—$R^{3a}$—, —$R^2$—$R^{3b}$—, or —$R^{3a}$—$R^2$—. For example, when $R^4$ is —$R^2$—$R^{3a}$—; $R^2$ is an ethylene chain, and n2 is five, then $R^4$ is —$CH_2$—$CH_2$—$(CH_2$—$CH_2$—$O)_5$—. Similarly, when $R^4$ is —$R^2$—$R^{3b}$—; $R^2$ is a methylene chain; and n2 is 8, then $R^4$ is —$CH_2$—$(O$—$CH_2$—$CH_2)_8$—.

$R^5$ is represented by —$R^9$—$R^6$—$R^9$—, and $R^6$ is represented by —$C(O)$—$NH$—$R^{3a}$—. $R^9$ is independently represented by $C_{1-4}$ alkyl.

$C_{1-4}$ alkyl represents a branched or unbranched, saturated or unsaturated carbon chain with a minimum of one carbon atom. The maximum number of carbon atoms is four. Preferably, the $C_{1-4}$ alkyl is a methylene or ethylene chain.

When $R^1$ is $R^5$, $R^9$ is independently a methylene or ethylene chain, and n2 is ten, then $R^1$ is represented by:

Y represents a reactive moiety, e.g., functional group. Y is —$CH$=$CH$—$C(O)OR^8$, —$CH$=$C(CH_3)$—$C(O)OR^8$, —$COOR^7$, —$N_3$, —$C$≡$C$—$R^8$, —$NH_2$, —$CHO$, —$OH$, -epoxide-$R^8$, —$SH$, or -maleimide. When $R^1$ is $R^{3a}$ or —$R^2$—$R^{3a}$—, Y is either —$CH$=$CH$—$C(O)OR^8$ or —$CH$=$C(CH_3)$—$C(O)OR^8$.

The variable $R^7$ is hydrogen, $C_{1-4}$ alkyl, or a moiety such that —$COOR^7$ is an activated ester. $R^8$ is hydrogen or $C_{1-4}$ alkyl.

Activated esters are esters which spontaneously react with an amino group. Common activated esters include nitrophenyl, pentafluorophenyl and succinimido esters. Nitrophenyl esters can be substituted at any position with one, tow, or three nitro groups, e.g., 2, 3, or 4 nitro, 3, 5 dinitro, or 2, 4, 6 trinitro. Preferably, the activated ester is an N-hydroxysuccinimide ester or a nitrophenyl ester. Compound 1d in Scheme 1 below contains an activated ester.

In another aspect of the invention, the curcumin derivatives are dimers represented by formula II, i.e., $Z^a$-$L^a$-$Y^a$-$(L^b)_{n3}$-$Y^b$-$L^c$-$Z^b$. In formula I, $Z^a$ and $Z^b$ are represented by:

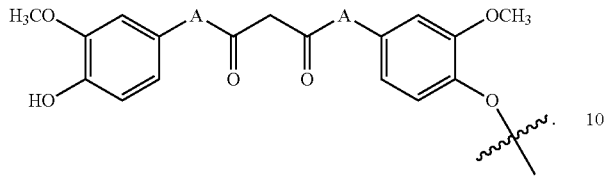

A, n1, n2, $R^2$, $R^{3a}$, $R^{3b}$, $R^5$, $R^6$, and $R^9$ are as described above.

$L^a$, $L^b$, and $L^c$ are independently —[C(O)]$_{n1}$—$R^{1a}$—. $R^{1a}$ is independently $R^2$, $R^4$, or $R^5$.

$Y^a$ and $Y^b$ are independently —COOR$^9$—, -triazolyl-, —NH—, —O—, or —S—S—. For example, $Y^a$ may represent —O— and $Y^b$ may represent -triazolyl-.

$R^{4a}$ is represented by —$R^2$—$R^{3b}$— or —$R^{1a}$—$R^2$—.

The variable n3 is independently 0 or 1. When n3 is 0, $Y^a$ and $Y^b$ are modified so that at least one covalent bond is formed between $Y^a$ and $Y^b$, and when n3 is 1, $L^b$ is modified so that at least one covalent bond is formed between $L^b$ and both $Y^a$ and $Y^b$.

Covalent bonds can be formed at any available atom on the triazolyl group.

In the present invention, various parameters are defined (e.g. A, L, Y, n1, n2, $R^1$, $R^2$, $R^3$, $R^4$). Within each parameter, more than one element (e.g. number, chemical moieties) are listed. It is to be understood that the instant invention contemplates embodiments in which each element listed under one parameter, may be combined with each and every element listed under any other parameter. For example, A is identified above as representing —CH$_2$—CH$_2$— or —CH═CH—. Y is identified above as being —CH═CH—C(O)OR$^8$, —CH═C(CH$_3$)—C(O)OR$^8$, —COOR$^7$, —N$_3$, —C≡C—R$^8$, —NH$_2$, —CHO, —OH, -epoxide-R$^8$, —SH, or -maleimide. Each element of A (—CH$_2$—CH$_2$— or —CH═CH—) can be combined with each and every element of Y (—CH═CH—C(O)OR$^8$, —CH═C(CH$_3$)—C(O)OR$^8$, —COOR$^7$, —N$_3$, —C≡C—R$^8$, —NH$_2$, —CHO, —OH, -epoxide-R$^8$, —SH, or -maleimide). For example, in one embodiment, A may be —CH$_2$—CH$_2$— and Y may be —N$_3$. Alternatively, A may be —CH═CH— and Y may be -epoxide-R$^8$, etc. Similarly, a third parameter is n1, in which the elements are defined as 0 or 1. Each of the above embodiments may be combined with each and every element of n1. For example, in the embodiment wherein A is —CH$_2$—CH$_2$— and Y is —COOR$^7$, n1 may be 1 (or any other number within the elements of n1).

In more specific embodiments, the invention relates to six curcumin monomers with the following modification at the phenolic group: a single acrylate or methacrylate, a single carboxylic acid, alkyne, N-Hydroxysuccinimide, a single azide group and Curcumin/tetrahydrocurcumin-triazole PEG, compounds 1a, 1b, 1c, 1d, 1e, and 1f, respectively, of Scheme 1.

Scheme 1 a)

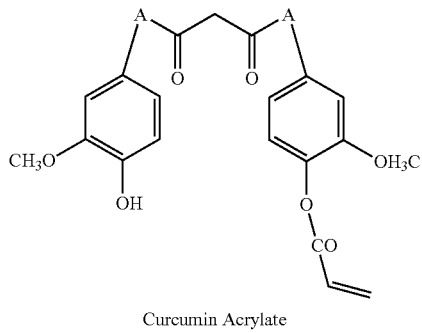

Curcumin Acrylate b)

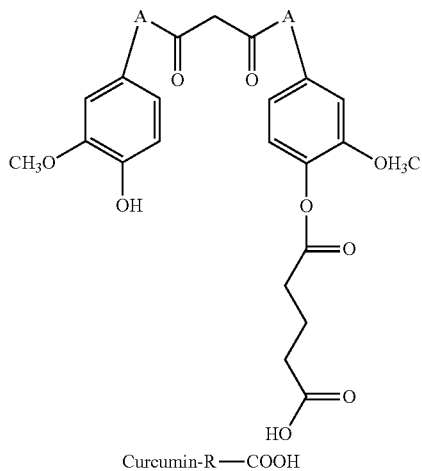

Curcumin-R—COOH c)

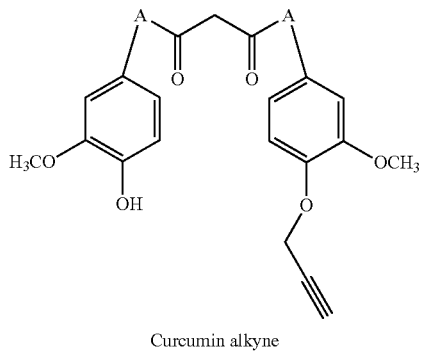

Curcumin alkyne d)

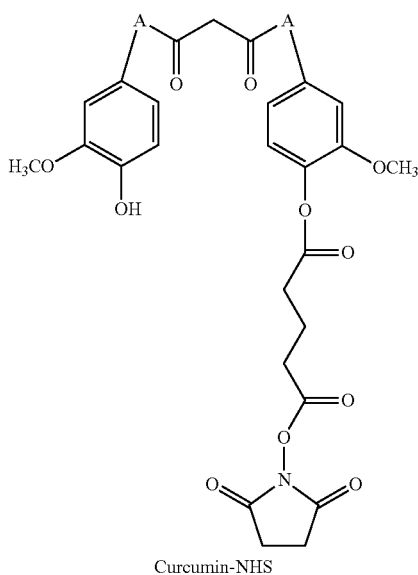

Curcumin-NHS e)

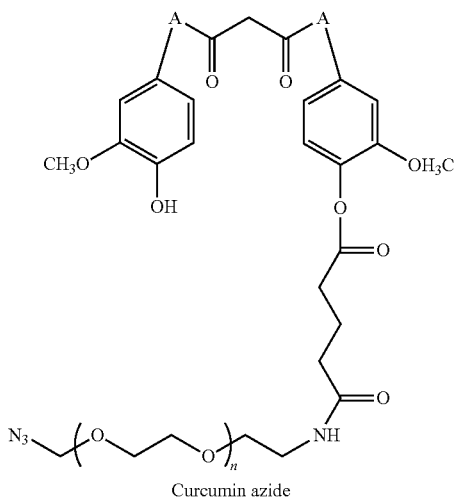

Curcumin azide f)

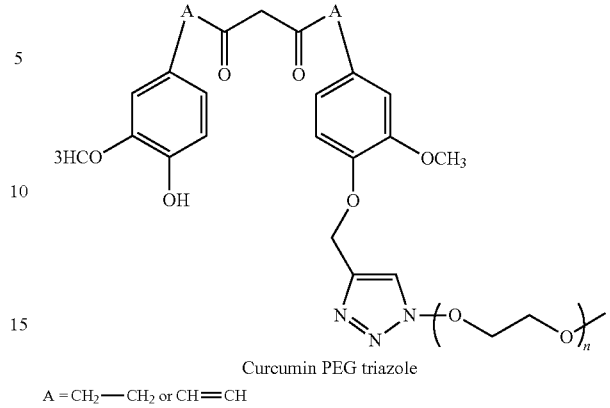

Curcumin PEG triazole

A = CH$_2$—CH$_2$ or CH=CH

In scheme 1.1, method for synthesizing the compounds of Scheme 1 are shown. The mono-carboxylic acid derivative of curcumin 1b is synthesized by reacting curcumin 1 with glutaric anhydride in the presence of base. Curcumin mono-azide derivative 1e is synthesized by an amide coupling reaction between curcumin mono-carboxylic acid 1b and an Amino-PEG Azide using 1,3-dicyclohexylcarbodiimide (DCC) at room temperature. The mono-alkyne derivative of curcumin 1c is synthesized by etherifying curcumin with propargyl bromide; K$_2$CO$_3$ is used as a base in DMF at room temperature. Etherification involving curcumin and propargyl bromide proceeded efficiently at room temperature. Mono-triazole-PEG derivative of curcumin 1f is synthesized by condensing mono-alkyne derivative of curcumin 1c with azidotrietheylene glycol under the Sharpless "click" condition (copper(II) sulfate and sodium ascorbate). A curcumin dimer is synthesized by reacting curcumin mono-alkyne derivative 1c with curcumin mono-azide derivative 1e using copper(II) sulfate and sodium ascorbate. The curcumin dimer, 1 g has two curcumin moieties connected by a triazole link and a PEG spacer. The dimer has two phenolic groups like the parent molecule 1.

The carboxylic acid group of 1b can be conjugated to proteins, biopolymers and synthetic polymers; the azide 1e and the alkyne derivative 1c can be attached to modified proteins and polymers via the "click" bioconjugation reaction.

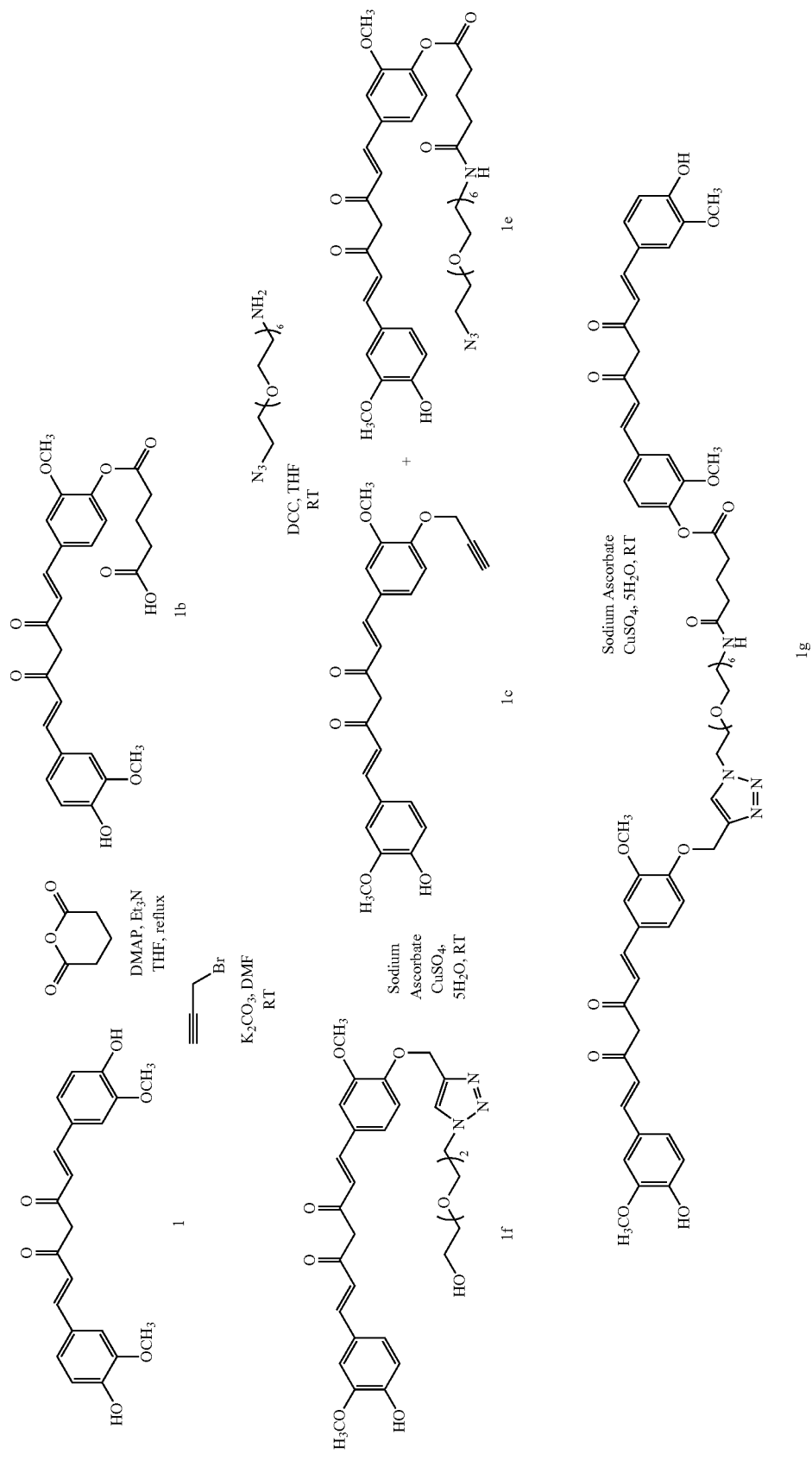

In another embodiment, bioconjugates can be synthesized using the curcumin derivatives of the invention. The reactive curcumin intermediate derivatives react with a variety of biopolymers to form macromolecular entities that can be useful in delivering the curcumin entities in vivo in a biocompatible and efficacious manner that enhances bioactivity.

For example, the curcumin intermediate derivatives can be reacted with polysaccharide containing pendant amines. This involves reaction of a carboxyl acid containing curcumin derivative with a polysaccharide containing pendant amine such as amino dextran shown in Scheme 4. See Hermanson, G. T. *Bioconjugate Techniques*; Academic Press: San Diego, Calif., 1996; Chapter 15, P 624. The portion of the Hermanson describing the synthesis of amino dextrans is herein incorporated by reference.

In another example, the curcumin intermediate derivatives can be reacted with proteins having amine residues, e.g., lysine. An example of this is given in Scheme 5. Note that a protein such as avidin containing lysine groups can react with a carboxyl modified curcumin to produce a bioconjugate with an amine linkage. A protein with lysine residues which is reacted with a carboxyl containing molecule is described in Raja, et al. "One-Pot Synthesis, Purification, and Formulation of Bionanoparticle-CpG Oligodeoxynucleotide Hepatitis B Surface Antigen Conjugate Vaccine via Tangential Flow Filtration." Bioconjugate Chem., 2007, 18, 285. The portion of the Raja, et al. reference describing Lysine modification of proteins is incorporated herein by reference. Other possible synthesis shown in Scheme 5 include either acetylene modified curcumin reacted with an azide modified protein or azide modified curcumin reacted with an acetylene modified protein, to a produce a curcumin protein bioconjugate having a triazole linkage.

Synthetic polymers can also be reacted with curcumin intermediate derivatives to form a synthetic polymer conjugate. For example, an amine pendant synthetic polymer such as poly 2 amino ethyl methacrylate can be reacted with a carboxyl containing curcumin derivative to produce a synthetic polymer conjugate with pendant curcumin moieties connected to the polymer using amide linkages. This can be found in Scheme 3. In another example, a carboxylic pendant synthetic polymer such as poly acrylic acid can be reacted with a amine containing curcumin derivative to produce a synthetic polymer conjugate with pendant curcumin moieties connected to the polymer using amide linkages.

Another class of synthetic polymer conjugates would contain polyethylene glycol (PEG). PEG containing polymers are typically water soluble and biocompatible. For example an azide terminated synthetic polymer such as PEG azide can be reacted with an alkyne containing curcumin derivative to produce a synthetic polymer conjugate with curcumin moieties connected to the polymer using triazole linkages 1f.

Similarly, the monomers can be polymerized to form curcumin polymers and copolymers. In Scheme 2, polymers and copolymers are produced by polymerizing curcumin/tetrahydrocurcumin acrylate and methacrylate by uncontrolled and controlled radical polymerization methods, e.g., atom transfer radical polymerization or RAFT.

Scheme 2 Example of Curcumin Acrylate Based Polymers

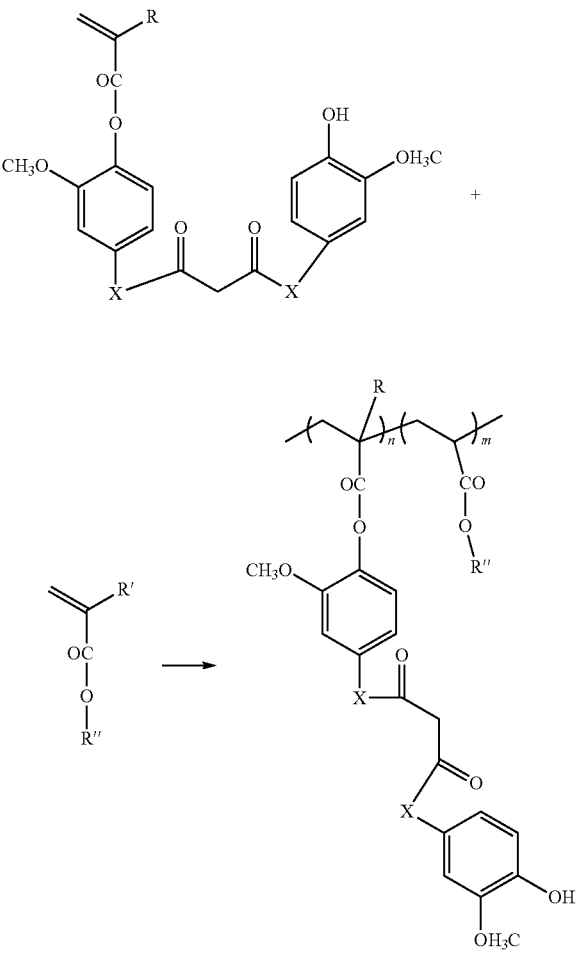

R = H or Me
R' = H or Me
X = CH$_2$—CH$_2$ or CH═CH

Scheme 2.1 Synthesis of curcumin acrylic acid homopolymer

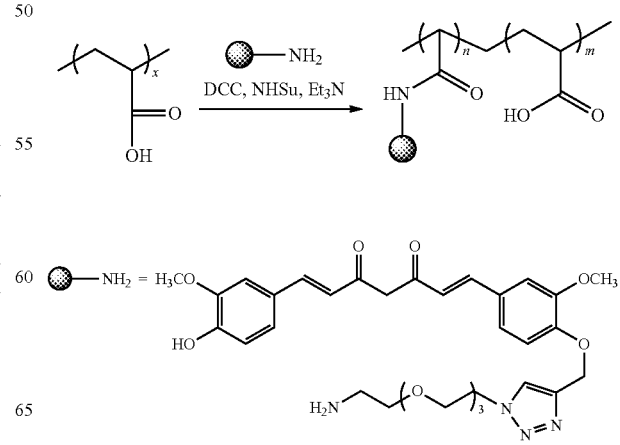

Scheme 2.2 Synthesis of curcumin polyacrylic acid conjugate

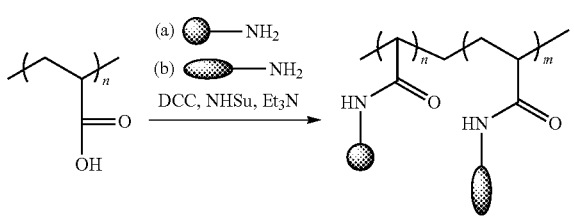

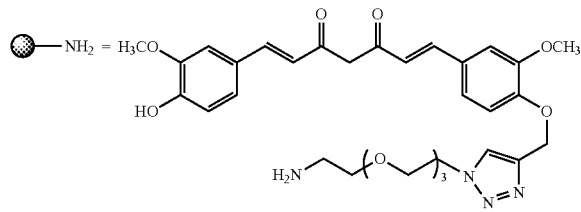

Synthetic polymers such as poly-2-aminoethyl methacrylate, polylysine, and dendrimers can be covalently modified with multiple amine functionalities. Polymers displaying multiple copies of azides or alkynes are shown in Scheme 3. Biopolymers including polysaccharides such as dextrans using the curcumin analogs 1a-1e are shown in Scheme 4. The chemical modification of proteins such as Protein A, Protein G, Protein L, antibodies, avidin, TAT peptide, collagen, elastin and bionanoparticles using the analogs 1a-1e and the resulting curcumin modified polymers are shown in Scheme 5. In another embodiment, the protein is streptavidin.

Scheme 3
Example of Curcumin Analog Modified Synthetic Polymer

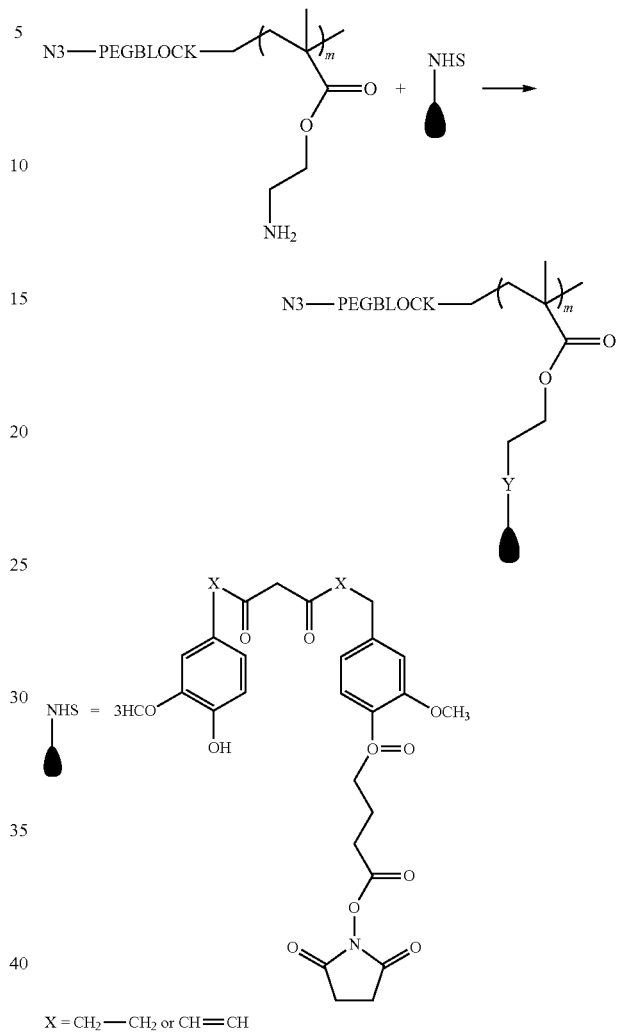

Scheme 4 Example of Curcumin Analog Modified Biopolymer

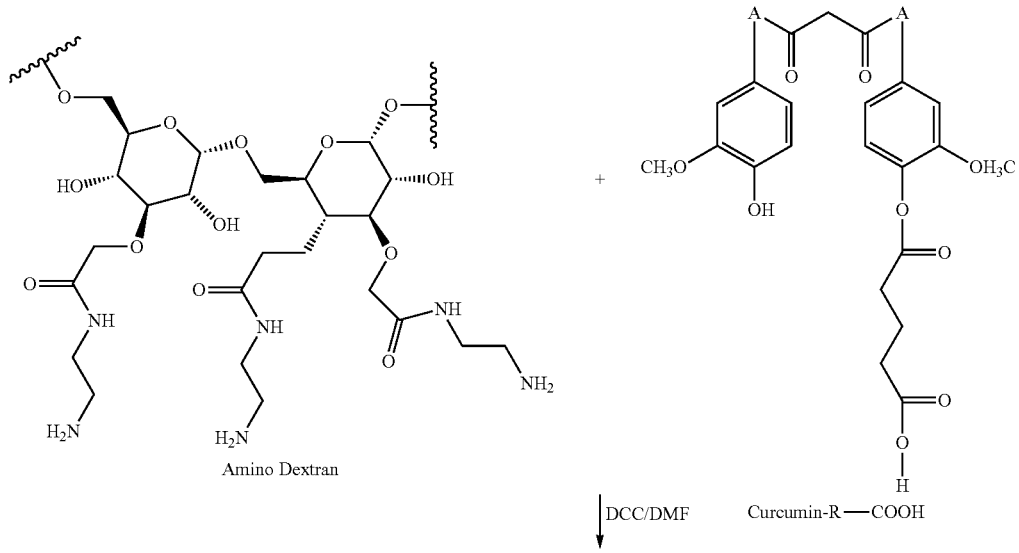

-continued

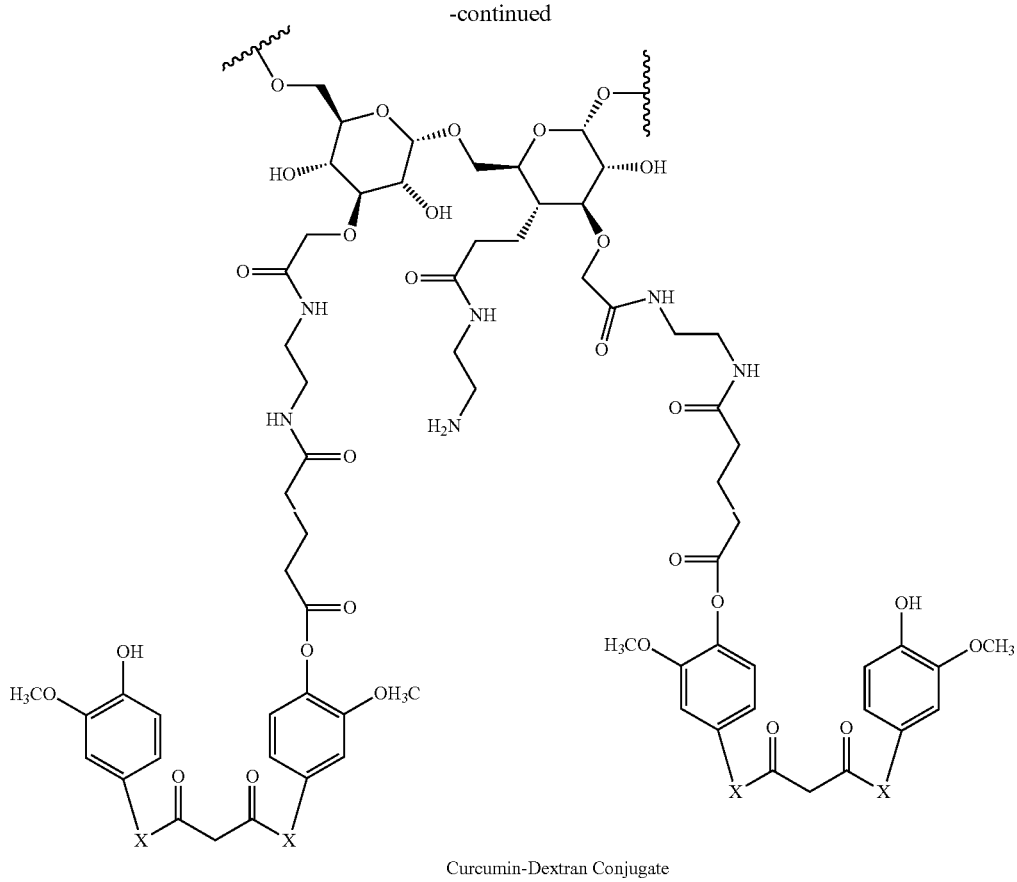

Curcumin-Dextran Conjugate

X = CH$_2$—CH$_2$ or CH=CH

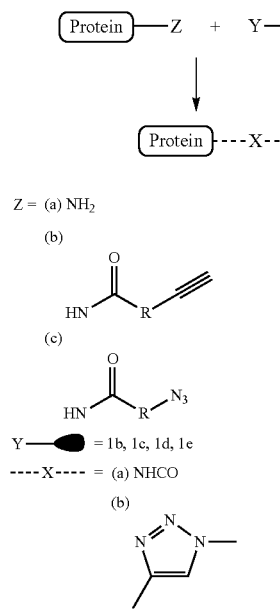

Scheme 5 Protein Curcumin Conjugates

Z = (a) NH$_2$
(b), (c)

Y—● = 1b, 1c, 1d, 1e
----X---- = (a) NHCO
(b)

Curcumin/THC and the THC and Curcumin derivatives of the invention are used as monomers in step condensation polymerization to produce both homopolymers and copolymers with comonomers, e.g., lactic acid, glycolic acids and amino acids, as well as any of the polymers mentioned above.

Polymers of lactic acid and glycolic acid have been reported in literature for biomedical applications.[25,13] Curcumin-modified dextrans are a typical example of curcumin modified polymers synthesized: Aminated dextrans were conjugated with Curcumin-R—COOH (1b) (Scheme 4). The resulting conjugates were characterized via size exclusion FPLC. The dextran curcumin conjugates elute at the same retention time as the starting amino dextran and has absorbance maximum at 430 nm, which arises from the conjugated curcumin.

Novel Curcumin/tetrahydrocurcumin dimers synthesized by connecting two curcumin molecules using spacers such as polyethylene glycol or a carbohydrate, the covalent connecting links between curcumin/tetrahydrocurcumin or its derivatives 1a-1e and the spacers being an ester, amide or triazole are claimed (Scheme 6), the dimer have two phenolic groups like the parent molecule along with improved water solubility and amplified biological activity.

Scheme 6 Curcumin-diester dimmer
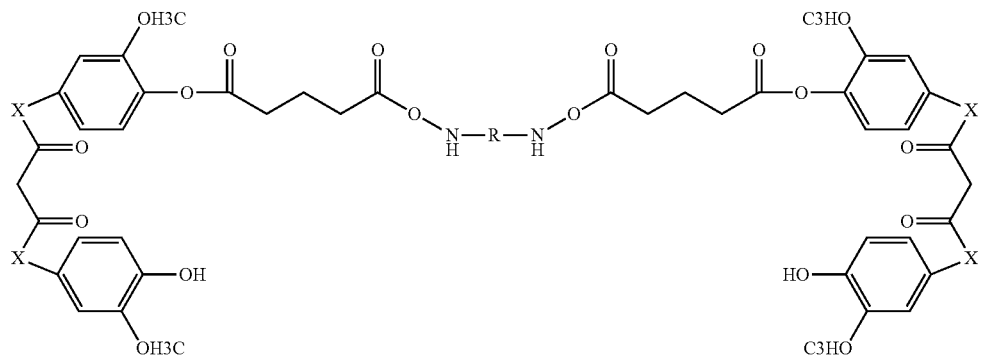
Curcumin Carboxylic acid based Symmetric Dimer
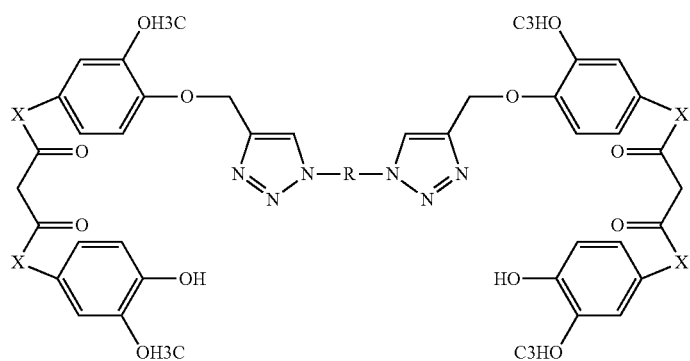
Curcumin Alkyne based Symmetric Dimer
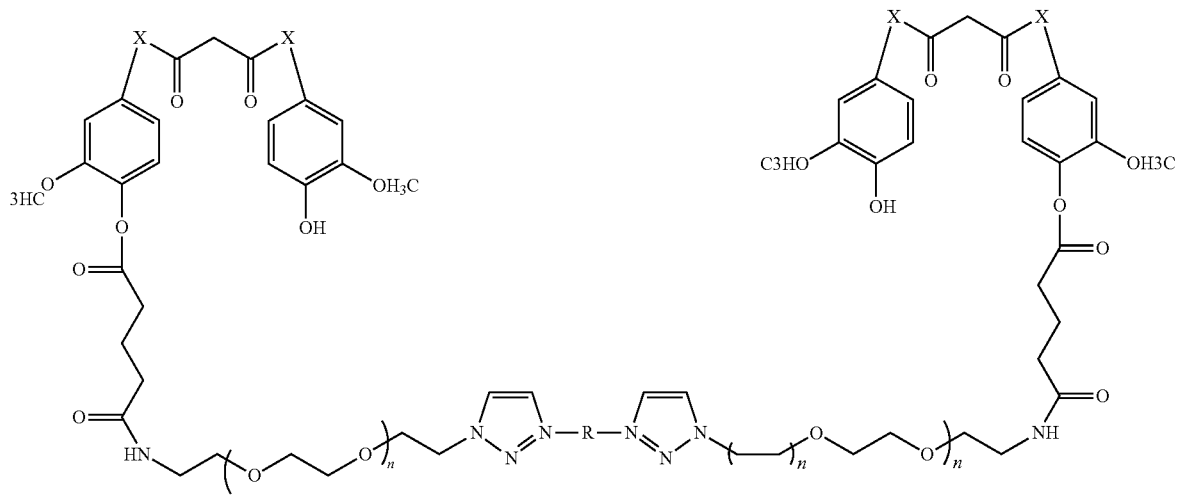
Curcumin Azide Based Symmetric Dimer
X = CH₂—CH₂ or CH=CH

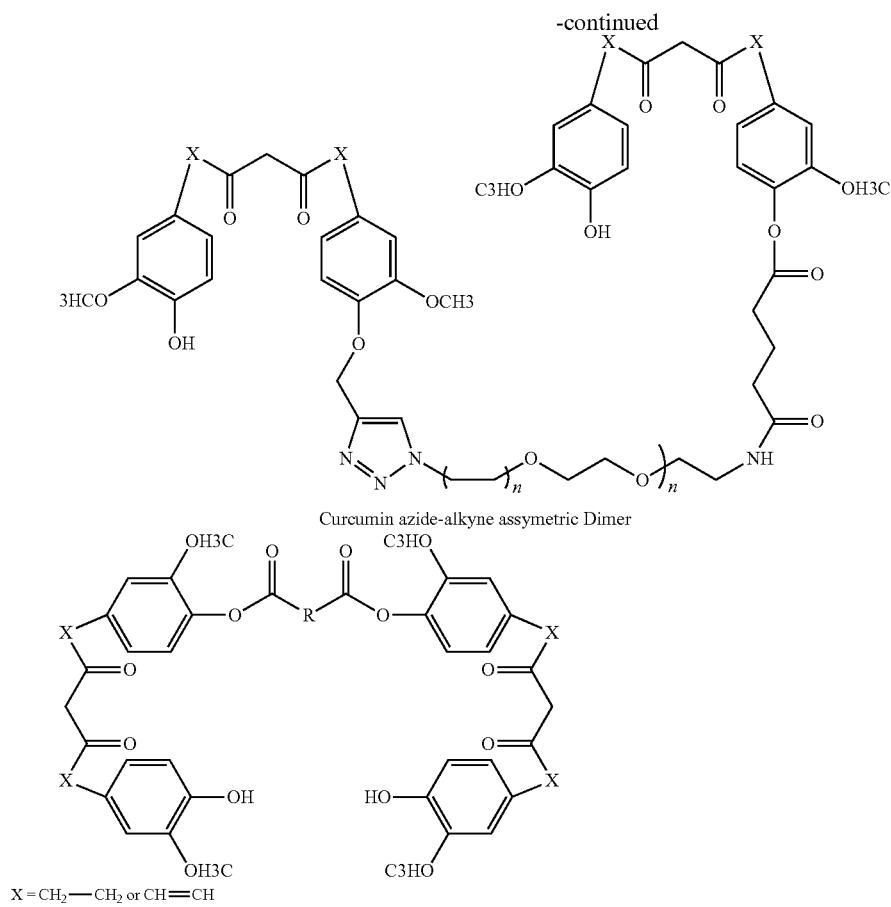

X = CH₂—CH₂ or CH=CH

Uses for Curcumin Derivatives
Bioconjugation Dyes and Imaging

Small molecule and polymeric curcumin derivatives were studied for use as bioconjugation dyes and for imaging applications with special emphasis on imaging amyloid plaque, in vitro and in vivo.

Curcumin has absorbance maximum at 430 nm and a molar extinction coefficient of 50,000; unlike many other dyes curcumin is completely non-toxic. Curcumin dyes can be excited at 460 nm to produce strong fluorescence emission. The same optics and technology (for techniques like confocal microscopy, fluorescence microcopy and gel imaging) which have been widely established and commercialized for the chromophore fluorescein can be employed for curcumin conjugates.

Inexpensive, eco-friendly dyes based on this 'green fluorescent chemical' for bioconjugation applications can be made where the biopolymer component is either a polysaccharide, a protein, DNA or RNA. Curcumin-R—COOH (1b) has been modified to produce the corresponding N-hydroxy succinimide (1d), curcumin-alkyne (1c) and curcumin azide (1e).

Each curcumin derivative is bioconjugated to create a biopolymer that can be used as an eco-friendly dye. For example, compounds 1b and 1d can be conveniently conjugated to the lysine residues of proteins, the azide and the alkyne derivatives can be attached to proteins via the 'click' bioconjugation reaction [6,7]. Compounds 1c and 1e have the advantage that unlike most reactive groups which are used for bioconjugation, alkyne and azide groups are stable in aqueous media (Scheme 5). The absorbance and fluorescence properties of these dyes are similar to the parent molecule. The molar extinction coefficient of some dyes are presented in Table 1.

TABLE 1

Molar Extinction Coeffecient of Curcumin Analogs

| Molecule | Molar Extinction Coeffecient |
|---|---|
| Curcumin-Carbxylic Acid | 57022 |
| Curcumin-Azide | 26764 |
| Curcumin-Alkyne | 29510 |
| Curcumin Acrylate | 46874 |

Alzheimer's and Prion Disease

Alzheimer's disease (AD) involves amyloid β accumulation, inflammation and oxidative damage of the brain. It has recently been shown using transgenic mouse model studies that injected curcumin crosses the blood-brain barrier and binds amyloid plaques. When fed to the mice with advanced amyloid accumulation, curcumin labeled the plaques and reduced amyloid levels and plaque burden [8].

The curcumin analogs in Scheme 1 were analyzed for their ability to label amyloid plaque. The results were good. Curcumin-dextran (50 nmol with respect to curcumin) was used to efficiently label human heart tissue (tissue slides were purchased from Sigma), the stained slides were imaged by confocal laser scanning microscopy.

The curcumin chromophore was excited with a 458 nm laser. Optics employed for the fluorescein chromophore will work efficiently for the curcumin derivatives of the claimed invention.

The superior solubility and polyvalent presentation of multiple copies of curcumin on polymeric scaffolds presented in Schemes 2-6 will enable more efficient labeling and dissolution of amyloid in vitro and in vivo. The curcumin modified polymers will have enhanced pharmacokinetics via increased plasma circulation time compared to small molecule analogs [10]. Many of the conjugates such as the TAT peptide-curcumin conjugate would cross the blood brain barrier effectively because it has been previously shown that TAT peptide helps in transporting quantum dots effectively across the blood brain barrier [11]. The curcumin dimers disclosed in this patent have two phenolic groups per molecule along with superior water and plasma solubility compared to the parent curcumin molecule.

Congo red is the current dye of choice to stain amyloid tissue [12]. However, Congo red has the disadvantage of being toxic. A much higher congo red dye concentration must be used for staining compared to the concentration of curcumin. Curcumin dyes have the advantage of being non-toxic.

Polarized light micrograph images of heart amyloid fibrils stained using dextran-curcumin conjugate and control Congo red stained sample prove that the curcumin analogs of the invention are excellent staining reagents. Small molecule analogs and curcumin modified polymers can be used for both diagnostic and therapeutic applications in vitro and in vivo in diseases associated with amyloid accumulation and uncontrolled protein aggregation including Alzheimer's and Mad Cows disease (prion disease) in mammals including *homo sapiens*.

For example, the ability of Curcumin-COOH (1b) to dissolve amyloid plaque can be seen. Amyloid plaque (Fibrils) were formed by adding 40 μL of the amyloidβ peptide Aβ-40 solution to a 96 well plate (40 μL per plate) and incubated for 3 days at 37° C. Either Curcumin-COOH or control buffer was added to the wells. The final concentrations were 8 μM Curcumin-COOH and 50 μG/mL Aβ-40. The Curcumin-COOH and control amyloid plaque samples were incubated for three more days at 37° C. The formation of plaque in the control samples was inferred from the UV spectrum of the control sample. Increased absorbance intensity throughout the UV-visible spectrum due to light scattering from the aggregates was observed. The UV spectrum of the Curcumin-COOH treated amyloid has a reduced absorbance relative to the control samples, aggregates are absent because the curcumin analog dissolves the plaque. The absorbance spectrum results were confirmed by studying the same samples used for the UV absorbance spectroscopy by Transmission electron microscopy. A network of fibers was observed in the control amyloid plaque samples whereas the fibrils were completely absent in the plaque samples treated with curcumin-COOH. This proves that the curcumin analogs covered in this patent are very effective in dissolving amyloid plaque.

Curcumin Analogs and Polymer Modified Curcumin Derivatives as Anticancer Agents

The small molecule curcumin analogs including curcumin dimers, curcumin polymers and curcumin modified polymers, typical examples shown in Schemes 1-6 of the present invention can be used for the treatment of cancer. The curcumin dimers and the polymer curcumin conjugates of the invention such as dextran-curcumin conjugates are more potent than the unmodified parent molecule curcumin in their ability to destroy Oligodendroglioma cells. Oligodendroglioma cells were treated with 50 micro molar concentration of curcumin and asymmetric curcumin dimer stained with DAPPI presented. The curcumin dimmer was observed as being superior in inducing apoptosis relative to the parent compound curcumin. Extensive apoptosis characterized by nuclear condensation (marked by bright blue DAPI staining) is observed in the cells exposed to curcumin dimer.

Data obtained at concentrations 20 μM and 50 μM show that the analogs cause considerable apoptosis. Very limited cell death is seen in human fibroblasts, which serve as a benign control cell line. The percentage of apoptosis is lower at higher concentrations (100 μM and more) as compared to that at 20 μM and 50 μM for all the compounds including curcumin because at higher concentration curcumin and analogs of the invention cause HOG cell necrosis. This alternate pathway of cell killing has been established via DNA laddering studies.

The blood vessels in tumors have abnormal architectures and impaired functional regulation. In particular vascular permeability in tumors is greatly enhanced for polymers which are retained in tumors for extended periods. This phenomenon is referred to as the "enhanced permeability and retention (EPR) effect." Macromolecules are therefore ideal for selective delivery to tumors. The EPR effect has facilitated the development of macromolecular drugs consisting of various polymer-drug conjugates (pendant type), polymeric micelles, and liposomes that exhibit better therapeutic efficacy and fewer side effects than the parent low-mol.-wt. compounds [15].

Dextran is non-toxic, it is a naturally occurring polysaccharide that is synthesized in yeast and bacteria. It has been used as a drug carrier to transport greater concentration of anti-neoplastic pharmaceuticals to tumor sites in vivo [16] and in synthesizing fluorescent tracers [17]. Curcumin-dextran conjugates have multiple copies of curcumin attached to dextran. These conjugated have been shown to have an amplified efficiency (a polyvalent response) in destroying cancer cells. The dextran-curcumin conjugates are also highly soluble in water and have the advantage of enhanced permeation and retention.

Cosmetic Applications

Curcumin is a powerful antioxidant [18] and skin protectant that has been used in oil-based cosmetic formulations in India. For example, curcumin is used in Sparsh™ and Vicco Turmeric Cream™. Tetrahydrocurcumin has been recently used as an additive in cosmetic formulations, because it has skin lightening and antioxidant properties and the aesthetic advantage that it is colorless unlike curcumin which is yellow colored [19, 20,21,22]. Most commercial cosmetic formulations are not oil-based. Incorporating curcumin or tetrahydrocurcumin into non-oil-based formulations at high concentrations is challenging because both molecules exhibit poor water solubility.

The novel small molecule and polymeric curcumin/tetrahydrocurcumin derivatives of the invention have improved water solubility and blending characteristics in cosmetic formulations. The polymeric curcumin derivatives have the added advantage that they would be retained for a longer periods on the skin. The polymeric derivatives have several copies of tetrahydrocurcumin/curcumin attached per polymer molecule, this polyvalent display of bioactive molecules leads to an amplified biological response of selectively killing cancer cells. The novel curcumin molecules of the invention may be incorporated into cosmetic formulations for prevention of melanoma by skin damage due to sunlight, for lightening skin color and for protecting the skin from free radical damage. Collagen and elastin are routinely used in cosmetic formulations for improving the texture of the skin and in anti-aging formulations [23-24]. The novel elastin/collagen conjugates with tetrahydrocurcumin/curcumin of the invention combine the powerful skin protectant, antioxidant and skin lightening properties of the curcumin/THC analogs along with the beneficial properties of collagen and elastin in a unique fashion. These compounds represent a new generation of active ingredients in cosmetic formulations.

EXAMPLES

The specific examples describe a preferred method for synthesizing the compounds of the present invention. The scope of this invention is not to be in any way limited by the examples set forth herein.

Reagent-grade solvents such as acetone and tetrahydrofuran were used without further purification. For High Performance Liquid Chromatography (HPLC), methylene chloride was used with Pure Solv™ solvent purification system. Curcumin was obtained from Acros-Organics. Copper acetate and sodium ascorbate were purchased from Sigma. Silica gel 60 F 254 plates for thin-layer chromatography (TLC) were purchased from Merck. Column chromatographic separations were carried out using silica gel (Fisher) with a particle size of 0.040-0.063 mm. Nuclear magnetic resonance (NMR) was recorded on Bruker Avance 600 (600 MHz) spectrometers. Mass spectra (ES-MS) were recorded on a LC/MS and Time Of Flight (TOF) mass spectrometer. U.V.-Visible spectra were recorded using a ChemStation Rev. A.10.01 from Agilent Technologies Amino Dextran 40, 70, 500 g/mole was purchased from Invitrogen. The FPLC-AKTA Purifier model 18-1400-00 with the Superose 6 10/300 GL column from Amersham Biosciences was used to analyze pure Amino Dextran 40 k, 70 k, and 500 k and the 40 k, 70 k, 500 k and other bio-conjugates. Deionized water was used as the primary solvent which was at a flow rate of 0.200 mL/min. Deionized water was used because Amino Dextran is very soluble in water, and this would minimize any possible interference with the absorbance.

Example 1

Synthesis of Mono-Methacryloyl Curcumin 1 and Di-Methacryloyl Curcumin 2

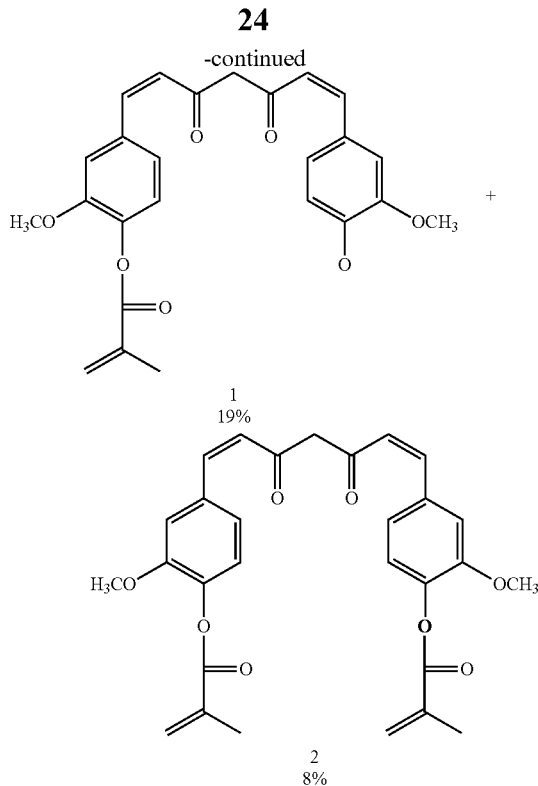

One g (2.71 mmol) curcumin was dissolved in 25 ml acetone, 0.37 g (3.66 mmol) Et$_3$N was added dropwise under ice temperature. Methacryloyl chloride 0.34 g (3.25 mmol) was added dropwise in 20 ml acetone. After the addition was complete, the reaction mixture was stirred for 95 minutes under 0° C. The temperature was then increased to 59° C. and refluxed overnight under nitrogen. The solution was evaporated under reduced pressure and a sticky solid was obtained. The residue was purified on column chromatography, eluting with CH$_2$Cl$_2$:hexane, 9:1. Yield 1.842 g (19% and 8%). $^1$H NMR (CDCl$_3$), δ (ppm): Compound 1, 2.08 (s, 3H); 3.87 (s, 3H); 3.95 (s, 3H); 5.78-5.83 (dd, 2H); 6.38 (s, 1H); 6.48-4.57 (dd, 2H); 6.93 (d, 1H); 7.05-7.16 (m, 6H); 7.60-7.62 (d, 2H). $^{13}$C NMR (CDCl$_3$), δ (ppm): 18.44; 55.93; 101.55; 109.60; 111.45; 114.83; 120.98; 121.75; 123.04; 123.31; 124.13; 127.53; 133.96; 135.38; 139.48; 141.09; 141.42; 146.78; 147.96; 151.52; 165.24; 181.86; 184.46. MS (ESI) calcd. for C$_{25}$H$_{24}$O$_7$ 436.45. found: 437.2 [M+H]$^+$, 459.1 [M$^+$+Na]. Compound 2, 2.08 (s, 6H); 3.85 (s, 6H); 5.78-5.86 (dd, 4H); 6.38 (s, 2H); 6.56-4.59 (d, 2H); 7.09-7.18 (m, 6H); 7.62-7.64 (d, 2H).

Example 2

Synthesis of Mono-Carbonyl Butanoic Acid 3

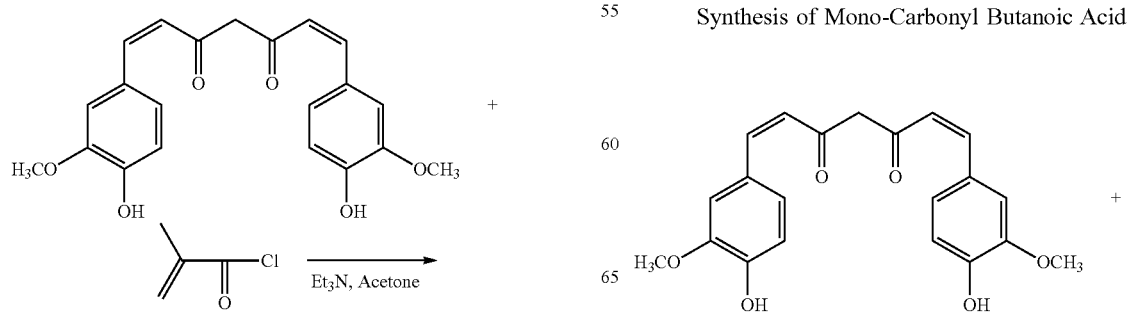

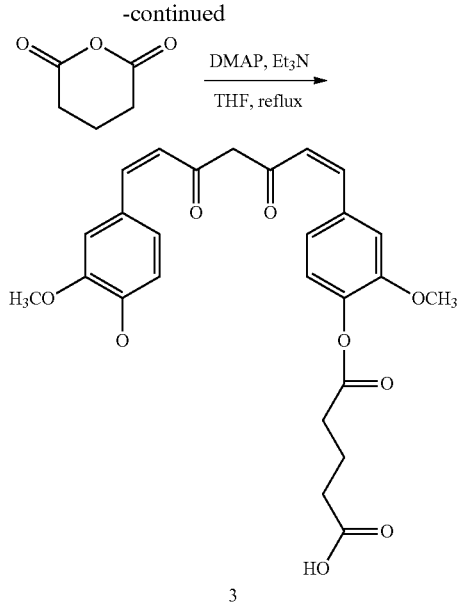

To a solution of 2.01 g (5.46 mmol) of curcumin, 112 mg (0.92 mmol) of DMAP, and 0.685 g (6 mmol) glutaric anhydride (95%) in 100 ml THF was added 1.33 ml (9.55 mmol) Et$_3$N. The reaction was stirred at reflux under argon overnight. Purified on column chromatography, eluting with CH$_2$Cl$_2$—CH$_2$Cl$_2$:MeOH, 95:5. Yield 84%. NMR $^1$H (CDCl$_3$), δ (ppm): compound (3), 1.97-2.14 (m, 2H); 2.43-2.79 (m, 4H); 3.87-3.95 (d, 6H); 5.83 (s, 2H); 6.45-6.59 (t, 2H); 6.91-7.18 (m, 6H); 7.57-7.65 (d, 2H). $^{13}$C NMR (CDCl$_3$), δ (ppm): 19.98; 32.76; 55.82; 101.61; 109.86; 111.36; 115.04; 120.95; 121.54; 123.05; 124.16; 127.35; 133.89; 139.38; 139.99; 141.06; 147.03; 148.22; 151.23; 170.98; 177.374; 181.73; 184.65. MS (ESI) calcd. for C$_{26}$H$_{26}$O$_9$: 482.48. found: 483.2 [M+H]$^+$.

See Robert E. Gawley; Mykhaylo Dukh; Claudia M. Cardona; Stephan H. Jannach; Denise Greathouse. *Org. Lettl.*, Vol. 7, No. 14, 2005.2953-2956.

Example 3

Synthesis of Mono-2-(2-(2-(2-(2-(2-azidoethoxy)ethoxy)ethoxy)ethoxy)ethoxy)ethylcarbamoyl butanoate-Curcumin 4

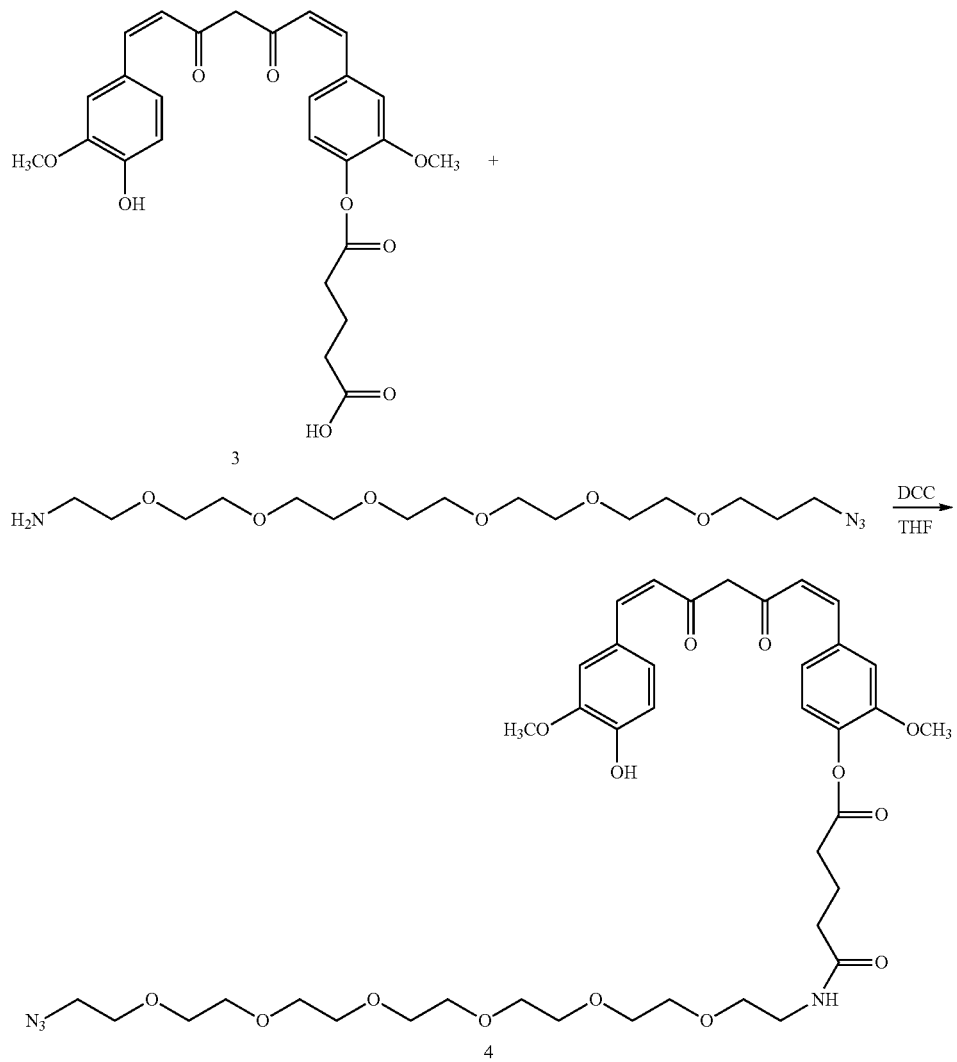

To a solution of 158 mg (0.45 mmol) of 3 in 3 mL dry THF at room temperature was added 206 mg (0.427 mmol) of O-(2-Aminoethyl)-O'-(2-azidoethyl)pentaethylene glycol and 96 mg (0.47 mmol) of 1,3-dicyclohexylcarbodiimide. The mixture was stirred at 25° C. overnight. The reaction mixture was then diluted with 10 mL of ethyl acetate, filtered to remove the urea byproduct, and the organic solvent was removed with a vacuum pump. The product was dissolved in methylene chloride and washed with water. Then, the organic phase was separated and dried with vacuum pump. The product was purified using column chromatography, eluting with $CH_2Cl_2$—$CH_2Cl_2$:MeOH, 95:5. Yield 29%. NMR $^1H$ (CDCl$_3$), δ (ppm): 1.72-1.78 (m, 2H); 2.35-2.38 (m, 2H); 2.66-2.70 (m, 2H); 3.37-3.66 (m, 28H); 3.88 (s, 3H); 3.95 (s, 3H); 6.40 (s, 1H); 6.48-6.57 (m, 2H); 6.93-6.94 (s, 1H); 7.05-7.27 (m, 6H); 7.59-7.63 (m, 2H). MALDI-TOF MS (calcd. for $C_{40}H_{54}N_4O_{14}$ 814.36). found: 837.38 [M$^+$+Na], 853.35 [M$^+$+K].

See Alwarsamy Jeganathan; Stewart K. Richardson; Rajarathnam S. Mani; Boyd E. Haley; David S. Watt. *J. Org. Chem.* 1986, 51, 5362-5367.

Example 4

Synthesis of Mono-Propargyl Curcumin 5

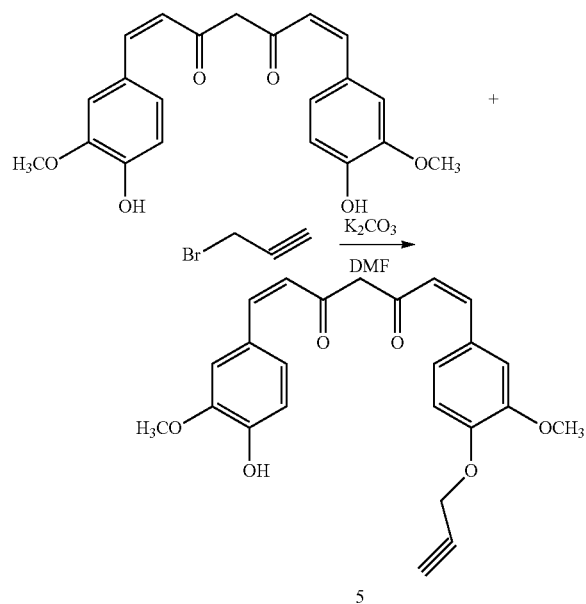

Curcumin (5 g, 13.57 mmol) and K$_2$CO$_3$ (1.88 g, 13.62 mmol) were dissolved in 60 mL DMF, and 1.62 g (13.61 mmol) of propargyl bromide was added. The mixture was stirred at room temperature under Ar for 49 h. H$_2$O was added to the mixture and solvent was removed under vacuum. The product was purified on column chromatography, eluting with $CH_2Cl_2$: hexane 50:50—$CH_2Cl_2$. Yield 47%. NMR $^1H$ (CDCl$_3$), δ (ppm): 2.54 (s, 1H); 3.94 (d, 6H); 4.81 (d, 2H); 5.82 (s, 1H); 5.93 (s, 1H); 6.47-6.52 (t, 2H); 6.93-7.15 (m, 6H); 7.59-7.61 (dd, 2H). MS (ESI) calcd. for $C_{24}H_{22}O_6$: 406.43. found: 407.2 [M+H]$^+$, 445.2 [M$^+$+K].

Example 5

Synthesis of Mono-2-(2-(2-(4-(methylene)-1H-1,2,3-triazol-1-yl)ethoxy)ethoxy)ethanol-curcumin 6

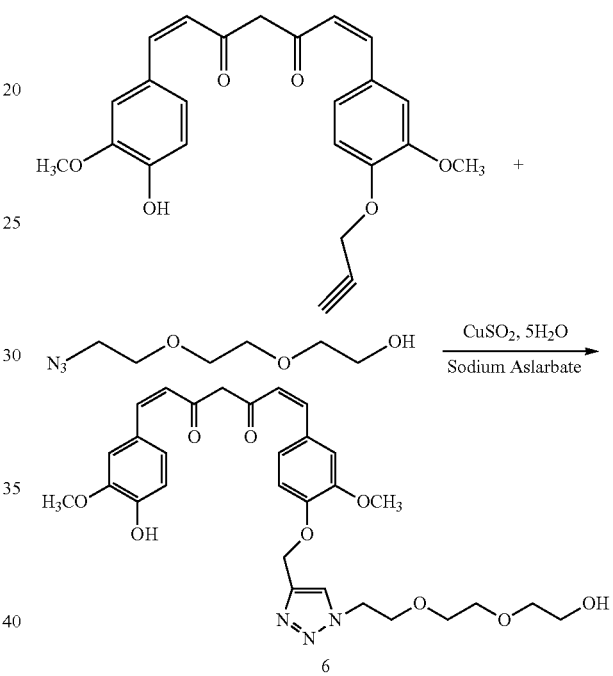

To a stirred solution of Mono-Propargyl Curcumin 5 (63 mg, 0.16 mmol) and 2-(2-(2-azidoethoxy)ethoxy)ethanol (46 mg, 0.26 mmol) in $^t$BuOH (1.1 mL) and CHCl$_3$ (0.3 mL) was added a prepared solution of Cu(OAc)$_2$ (8 mg, 0.03 mmol) and sodium ascorbate (13 mg, 0.07 mmol) in H$_2$O (1.3 mL). After vigorous stirring overnight the solvent was removed under vacuum. The mixture was dissolved in CHCl$_3$, washed with H$_2$O and the organic phase was separated, dried over Na$_2$SO$_4$ and evaporated. Purification was performed by column chromatography, eluting with $CH_2Cl_2$—$CH_2Cl_2$: MeOH 98:2. Yield 26%. NMR $^1H$ (CDCl$_3$), δ (ppm): 3.55-3.60 (m, 8H); 3.72-3.72 (t, 3H); 3.87-3.94 (m, 8H); 4.54-4.55 (t, 2H); 5.80 (s, 1H); 6.07 (s, 1H); 6.46-6.50 (dd, 2H); 6.92-6.94 (d, 1H); 7.05-7.12 (m, 5H); 7.56-7.60 (q, 2H); 7.92 (s, 1H).). MS (ESI) calcd. for $C_{30}H_{35}N_3O_9$: 581.61. found: 582.3 [M+H]$^+$, 604.3 [M$^+$+Na], 620.3 [M$^+$+K].

See Maarten Ijsselstijn and Jean-Christophe Cintrat. *Tetrahedron.* 2006, 62, 3837-3842.

Example 6

Synthesis of (2-(2-(2-(2-(2-(2-(2-(4-methylene)-1H-1,2,3-triazol-1-yl)ethoxy)ethoxy)ethoxy)ethoxy)ethoxy)ethoxy)ethylcarbamoyl butanoate curcumin dimer 7

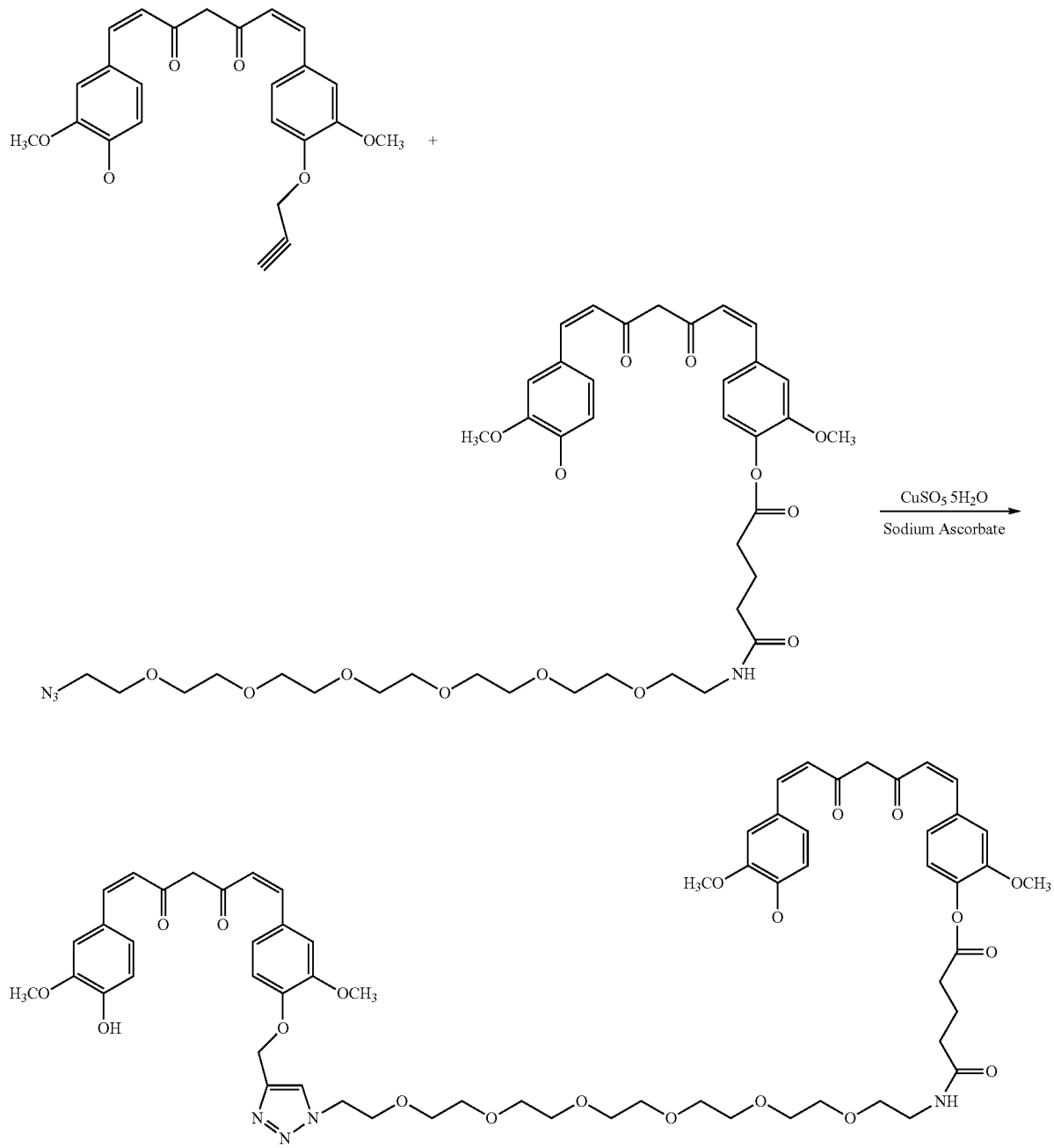

Compound 7 was synthesized using the same procedure employed for the synthesis of 6. The product was isolated in 41% yield. NMR $^1$H (CDCl$_3$), δ (ppm): 1.60-1.63 (bd, 2H); 2.26-2.29 (t, 2H); 2.47-2.49 (t, 2H); 3.41-3.42 (t, 2H); 3.53-3.63 (m, 26H); 3.86-3.95 (m, 12H); 4.54-4.55 (d, 4H); 5.33 (s, 2H); 6.55-6.56 (bd, 4H); 6.94-7.11 (bm, 12H); 7.59 (s, 4H); 7.87 (s, 1H).). MALDI-TOF MS (calcd. for $C_{64}H_{76}N_4O_{20}$ 1220.51). found: 1243.52 [M$^+$+Na], 1259.47 [M$^+$+K].

See Maarten Ijsselstijn and Jean-Christophe Cintrat. *Tetrahedron.* 2006, 62, 3837-3842.

Example 7

Synthesis of Dextran 40K Mono-Carbonyl Butanoic Acid Curcumin Conjugate 1

Dextran 32 mg ($8\times10^{-4}$ mmol), mono-carbonyl butanoic acid curcumin 69 mg ($1.4\times10^{-3}$ mmol) and DCC (1,3-dicyclohexylcarbodiimide) 48 mg ($2.3\times10^{-3}$ mmol) were dissolved in 1 ml dry DMSO. The reaction was stirred for 24 h at reflux under argon. The solution was filtered, dialyzed with SnakeSkin pleated dialysis tubing with Millipore water, centrifuged and lyophilized. A cotton candy-like product (31 mg) was obtained in quantitative yield. NMR $^1$H (D$_2$O), δ (ppm): compound 1, 1.77 (m,); 1.93-2.04 (bm); 2.17-2.21 (m); 2.86-2.91 (m); 3.52-3.60 (m); 3.72-3.78 (m); 3.92-4.01 (dd); 5.00 (d). Number of Curcumin molecules attached per polymer molecule is 10 (Estimated from UV spectroscopy using the extinction coefficient for Curcumin-COOH).

Example 8

Synthesis of Dextran 70K Mono-Carbonyl Butanoic Acid Curcumin Conjugate 2

Dextran 122 mg ($3\times10^{-3}$ mmol), Mono-carbonyl butanoic acid curcumin 16 mg ($3.3\times10^{-4}$ mmol) and DCC (1,3-dicyclohexylcarbodiimide) 10 mg ($4.8\times10^{4}$ mmol) were dissolved in 5.5 ml dry DMSO. The reaction was stirred for 24 h at reflux under argon The solution was filtered, dialyzed with SnakeSkin pleated dialysis tubing with Millipore water, centrifuged and lyophilized. The product resembled cotton candy and the yield was quantitative. NMR $^1$H (D$_2$O), δ (ppm): compound 2, 1.35-1.39 (m); 1.67 (m,); 1.78-1.92 (bm); 2.33 (bm); 2.41-2.44 (t); 3.53-3.56 (t); 3.59-3.61 (m); 3.73-3.79 (m); 3.93-4.02 (dd); 5.00 (d). Number of Curcumin molecules attached per polymer molecule is 22 (Estimated from UV spectroscopy using the extinction coefficient for Curcumin-COOH).

CITATIONS

1. Chattopadhyay, Ishita; Biswas, Kaushik; Bandyopadhyay, Uday; Banerjee, Ranajit K. Turmeric and curcumin: biological actions and medicinal applications. *Current Science* (2004), 87(1), 44-53.
2. Agarwal, Bharat, B.; and Shishodia, S. Molecular targets of dietary agents for the prevention and therapy of cancer. *Biochemical Pharmocology* (2006), 71, 1397-1421.
3. Leyon, P. V.; Kuttan, G. Studies on the role of some synthetic curcuminoid derivatives in the inhibition of tumour specific angiogenesis. *Journal of Experimental & Clinical Cancer Research* (2003), 22(1), 77-83.
4. Nurfinal, A. N.; Reksohadiprodjo, M. S.; Timmerman, H.; Jenie, U. A.; Sugiyant, D.; van der Goot, H. Synthesis of some symmetrical curcumin derivatives and their antiinflammatory activity. *Eur J Med Chem* (1997) 32, 321-328.
5. Mizushina, Y.; Ishidoh, T.; Takeuchi, T.; Shimazaki, N.; Koiwai, O.; Kuramochi, K.; Kobayashi, S.; Sugawara, F.; Sakaguchi, K.; Yoshida, H. Monoacetylcurcumin: A new inhibitor of eukaryotic DNA polymerase and a new ligand for inhibitor-affinity chromatography, *Biochemical and Biophysical Research Communications* (2005) 337, 1288-1295
6. Raja, Krishnaswami S./Gupta, Sayam Sen; Kaltgrad, Eiton; Strable, Erica; Finn, M. G. Virus-glycopolymer conjugates by copper(I) catalysis of atom transfer radical polymerization and azide-alkyne cycloaddition. *Chemical Communications* (2005), (34), 4315-4317.
7. Wang, Qian; Chan, Timothy R.; Hilgraf, Robert; Fokin, Valery V.; Sharpless, K. Barry; Finn, M. G. Bioconjugation by copper(I)-catalyzed azide-alkyne [3+2] cycloaddition. *Journal of the American Chemical Society* (2003), 125(11), 3192-3193.
8. Yang, Fusheng; Lim, Giselle P.; Begum, Aynun N.; Ubeda, Oliver J.; Simmons, Mychica R.; Ambegaokar, Surendra S.; Chen, Pingping; Kayed, Rakez; Glabe, Charles G.; Frautschy, Salley A.; and Cole, Gregory M. Curcumin Inhibits Formation of Amyloid Oligomers and Fibrils, Binds Plaques, and Reduces Amyloid in Vivo. *Journal of Biol. Chem.* (2005) 280(7), 5892-5901.
9. Cheng, A. L.; Hsu, C. H.; Lin, J. K.; Hsu, M. M; Ho, Y. F; Shen, T. S; Ko, J. Y; Lin, J. T; Lin, B. R; Wu, M. S.; Yu, H. S.; Jee, S. H.; Chen, G. S.; Chen, T. M.; Chen, C. A.; Lai, M. K.; Pu, Y. S.; Pan, M. H.; Wang, Y. J.; Tsai, C. C.; and Hsieh, C. Y. Phase 1 Clinical Trial of Curcumin, a Chemopreventive Agent, in Patients with Highrisk of Pre-malignant Lesions. *Anticancer Res* 21: 2895-2001.
10. Harris, J. M. *Poly (ethylene glycol) chemistry*, Plenum Press, New York
11. Santra, S.; Yang, H.; Stanley, J. T.; Holloway, P. H; Moudgil, B. M.; Walter, G.; and Mericle, R. A. Rapid and effective labeling of brain tissue using TAT-conjugated CdS:Mn/ZnS quantum dots. *Chem Commun* (2005) 3144-3146.
12. Puchtler, H., Sweat, F., and Levine, M. (1962) *J. Histochem. Cytochem.* 10, 355-364
13. Gilding, D. K., A. M. Reed (December 1979). "Biodegradable polymers for use in surgery-polyglycolic/poly (lactic acid) homo- and copolymers: 1". *Polymer* 20: 1459-1464.
14. Kurzrock, R.; Li, L.; Mehta, K.; Aggarwai, B. B. Liposomal curcumin for treatment of cancer. PCT Int. Appl. (2004), 66 pp. CODEN: PIXXD2 WO 2004080396 A2 20040923
15. Maeda, H.; Greish, K.; Fang, J. The enhanced permeability and retention effect and polymeric drugs: a paradigm shift for cancer chemotherapy in the 21st century. *Advances in Polymer Science* (2006), 193 (Polymer Therapeutics II), 103-121. Publisher: Springer GmbH.
16. Heindel, N. D.; Zhao, H., Leiby, J., VanDongen, J. M.; Lacey, C. J.; Lima, D. A.; Shabsoug, B. and Buzby, J. H. Hydrazide pharmaceuticals as conjugates to polyaldehyde dextran: Synthesis characterization and stability. *Bioconjugate. Chem.* (1990) 1, 77-82.
17. Gee, K. R.; Weinberg, E. S.; Kozlowski, D. J. Caged Q-rhodamine dextran: a new photo-activated fluorescent tracer. *Bioorganic & Medicinal Chemistry Letters* (2001), 11(16), 2181-2183.
18. Jovanovic, V.; Boone, C. W.; Steenken, S.; Trinoga, M. and Kaskey, R. B. How Curcumin Works Preferentially with Water Soluble Antioxidants *J. Am. Chem. Soc.* (2001), 123, 3064-3068
19. Hasegawa, K; Maeda, N. Skin-lightening cosmetics containing tetrahydrocurcuminoids. (Shiseido Co., Ltd., Japan) (2004), 38 pp. CODEN: JKXXAF JP 2004115381 A2 20040415 Patent written in Japanese. Application: JP 2002-277174 20020924. Priority: CAN 140:326645 AN 2004:310050 CAPLUS
20. Rieks, A.; Kaehler, M.; Kirchner, U.; Wiggenhorn, K.; Kinzer, M. Preparation of novel curcumin/tetrahydrocurcumin derivatives for use in cosmetics, pharmaceuticals and for nutrition. (Andre Rieks—Labor fuer Enzymtechnologie G.m.b.h., Germany). PCT Int. Appl. (2004), 54 pp. CODEN: PIXXD2 WO 2004031122 A1 20040415

21. Use of antioxidants for the preparation of pharmaceutical or cosmetic compositions for protecting the skin from damages by infrared-radiation. (Stada Arzneimittel A.-G., Germany). Eur. Pat. Appl. (2005), 12 pp. CODEN: EPXXDW EP 1591104 A1 20051102

22. Cross regulin composition of turmeric-derived Tetrahydrocurcuminoids for skin lightening and protection against UVB rays Sabinsa Corporation, U.S. Pat. No. 665332723. Method for sterilizing a native collagen in liquid medium, sterile native collagen obtained, compositions containing it and uses, Mansour Hamza, Octapharma Agency, Patent Number US 2002061842.

24. Partridge, S. Elastin, Adv. In Protein Chemistry, Academic Press, New York, (1962), 1Z, 227.

25. Kricheldorf, H. R. Syntheses and application of polylactides. Chemosphere (2001), 43(1), 49-54.

We claim:

1. A curcumin derivative having the formula I:

Z-$L_n$-Y  (I)

wherein:
Z is represented by:

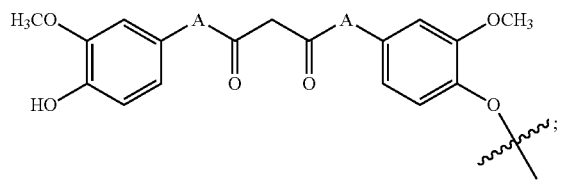

A is —$CH_2$—$CH_2$— or —CH=CH—;
L is —[C(O)]$_{n1}$—$R^1$—;
n is 0 or 1;
n1 is 1;
$R^1$ is $R^2$, $R^{3a}$, $R^4$, or $R^5$;
$R^2$ is a saturated or unsaturated, branched or unbranched hydrocarbyl with 1 to 18 carbon atoms;
$R^{3a}$ is —($CH_2$—$CH_2$—O)$_{n2}$—;
$R^{3b}$ is —(O—$CH_2$—$CH_2$)$_{n2}$—;
n2 is an integer between 1 and 2,000;
$R^4$ is —$R^2$—$R^{3a}$—, —$R^2$—$R^{3b}$—, or —$R^{3a}$—$R^2$—;
$R^5$ is —$R^9$—$R^6$—$R^9$—;
$R^6$ is —C(O)—NH—$R^{3a}$—;
Y is —CH=CH—C(O)$OR^8$, —CH=C($CH_3$)—C(O)$OR^8$, —COOR$^7$, —$N_3$, —C≡C—$R^8$, —$NH_2$, —CHO, —OH, -epoxide-$R^8$, or —SH;
with the proviso that when n is 0, Y is —CH=CH—C(O)$OR^8$ or —CH=C($CH_3$)—C(O)$OR^8$;
with the proviso that when $R^1$ is $R^{3a}$ or —$R^2$—$R^{3a}$—, Y is —CH=CH—C(O)$OR^8$ or —CH=C($CH_3$)—C(O)$OR^8$;
$R^7$ is $C_{1-4}$ alkyl, or a moiety such that —COOR$^7$ is an activated ester;
$R^8$ is hydrogen or $C_{1-4}$ alkyl; and
$R^9$ is independently $C_{1-4}$ alkyl.

2. The curcumin derivative according to claim 1, wherein:
$R^2$ is a saturated or unsaturated, unbranched hydrocarbyl with 1 to 18 carbon atoms;
n2 is an integer between 1 and 50;
$R^7$ is $C_{1-2}$ alkyl, or a moiety such that —COOR$^7$ is an activated ester;
$R^8$ is hydrogen or $C_{1-2}$ alkyl; and
$R^9$ is $C_{1-2}$ alkyl.

3. The curcumin derivative according to claim 2, wherein:
$R^2$ is a saturated, unbranched hydrocarbyl with 1 to 5 carbon atoms; and
Y is —CH=CH—C(O)$OR^8$, —CH=C($CH_3$)—C(O)$OR^8$, —COOR$^7$, —$N_3$, or —C≡C—$R^8$.

4. The curcumin derivative according to claim 1, wherein the maximum value for n2 is 12.

5. The curcumin derivative according to claim 1, wherein the activated ester is an N-hydroxysuccinimide ester or a nitrophenyl ester.

6. A curcumin derivative, selected from the group consisting of:

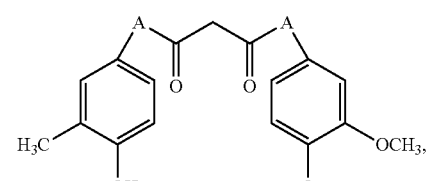

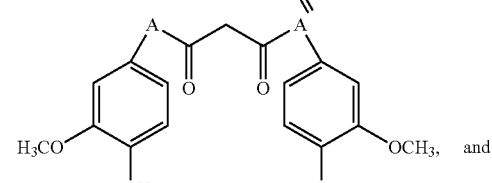
and

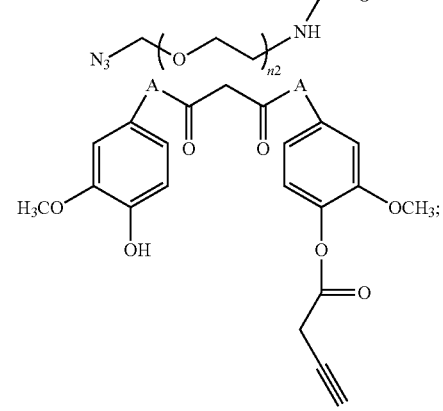

wherein n2 is an integer between 1 and 2,000, and wherein A is —$CH_2$—$CH_2$— or —CH=CH—.

7. The curcumin derivative according to claim 1, wherein Y is —CH=CH—C(O)$OR^8$ or —CH=C($CH_3$)—C(O)$OR^8$.

8. The curcumin derivative according to claim 1, wherein Y is —C≡C—$R^8$.

9. The curcumin derivative according to claim 1, wherein Y is —$N_3$.

10. The curcumin derivative according to claim 1, wherein Y is $NH_2$.

11. A curcumin derivative that is curcumin acrylate, selected from the group consisting of:

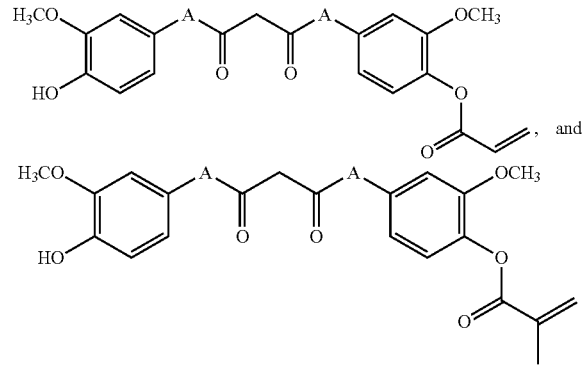
, and wherein A is —CH$_2$—CH$_2$— or —CH=CH—.

12. A curcumin derivative having the formula:

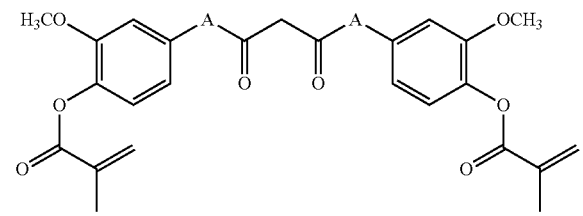

wherein A is —CH$_2$—CH$_2$— or —CH=CH—.

13. A curcumin derivative having the formula I:

$$Z\text{-}L_n\text{-}Y \qquad (I)$$

wherein:
Z is represented by:

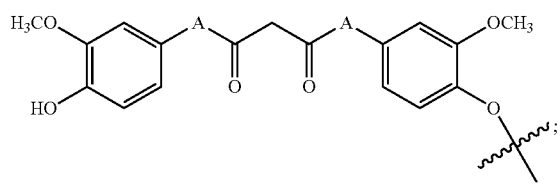

A is —CH$_2$—CH$_2$— or —CH=CH—;
L is —[C(O)]$_{n1}$—R$^1$—;
n is 0 or 1;
n1 is 0 or 1;
R$^1$ is R$^2$, R$^{3a}$, R$^4$, or R$^5$;
R$^2$ is a saturated or unsaturated, branched or unbranched hydrocarbyl with 1 to 18 carbon atoms;
R$^{3a}$ is —(CH$_2$—CH$_2$—O)$_{n2}$—;
R$^{3b}$ is —(O—CH$_2$—CH$_2$)$_{n2}$—;
n2 is an integer between 1 and 2,000;
R$^4$ is —R$^2$—R$^{3a}$—, —R$^2$—R$^{3b}$—, or —R$^{3a}$—R$^2$—;
R$^5$ is —R$^9$—R$^6$—R$^9$—;
R$^6$ is —C(O)—NH—R$^{3a}$—;
Y is —CH=CH—C(O)OR$^8$, —CH=C(CH$_3$)—C(O)OR$^8$, —N$_3$, —C≡C—R$^8$, or —NH$_2$;
with the proviso that when n is 0, Y is —CH=CH—C(O)OR$^8$ or —CH=C(CH$_3$)—C(O)OR$^8$;
with the proviso that when R$^1$ is R$^{3a}$ or —R$^2$—R$^{3a}$—, Y is —CH=CH—C(O)OR$^8$ or CH=C(CH$_3$)—C(O)OR$^8$;
R$^8$ is hydrogen or C$_{1-4}$ alkyl; and
R$^9$ is independently C$_{1-4}$ alkyl.

14. A curcumin derivative having the formula I:

$$Z\text{-}L_n\text{-}Y \qquad (I)$$

wherein:
Z is represented by:

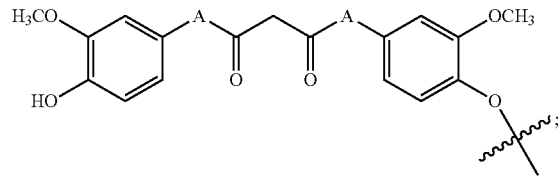

A is —CH$_2$—CH$_2$— or —CH=CH—;
L is —[C(O)]$_{n1}$—R$^1$—;
n is 0 or 1;
n1 is 0 or 1;
R$^1$ is R$^2$, R$^{3a}$, R$^4$, or R$^5$;
R$^2$ is a saturated or unsaturated, branched or unbranched hydrocarbyl with 1 to 18 carbon atoms;
R$^{3a}$ is —(CH$_2$—CH$_2$—O)$_{n2}$—;
R$^{3b}$ is —(O—CH$_2$—CH$_2$)$_{n2}$—;
n2 is an integer between 1 and 2,000;
R$^4$ is —R$^2$—R$^{3a}$—, —R$^2$—R$^{3b}$—, or —R$^{3a}$—R$^2$—;
R$^5$ is —R$^9$—R$^6$—R$^9$—;
R$^6$ is —C(O)—NH—R$^{3a}$—;
Y is —CHO, —OH, -epoxide-R$^8$, or —SH;
with the proviso that when n is 0, Y is —CH=CH—C(O)OR$^8$ or —CH=C(CH$_3$)—C(O)OR$^8$;
with the proviso that when R$^1$ is R$^{3a}$ or —R$^2$—R$^{3a}$—, Y is —CH=CH—C(O)OR$^8$ or CH=C(CH$_3$)—C(O)OR$^8$;
R$^8$ is hydrogen or C$_{1-4}$ alkyl; and
R$^9$ is independently C$_{1-4}$ alkyl.

* * * * *

UNITED STATES PATENT AND TRADEMARK OFFICE
CERTIFICATE OF CORRECTION

PATENT NO. : 9,447,023 B2  
APPLICATION NO. : 13/942606  
DATED : September 20, 2016  
INVENTOR(S) : Raja et al.

Page 1 of 1

It is certified that error appears in the above-identified patent and that said Letters Patent is hereby corrected as shown below:

Column 1, Line 66:
Delete: "ant parasitic,"
Insert: -- antiparasitic, --

Column 4, Line 63:
Delete: "tow,"
Insert: -- two, --

Column 31, Line 30:
Delete: "argon The"
Insert: -- argon. The --

Signed and Sealed this
Thirtieth Day of May, 2017

Michelle K. Lee
*Director of the United States Patent and Trademark Office*